United States Patent
Earl et al.

(10) Patent No.: US 10,254,277 B2
(45) Date of Patent: Apr. 9, 2019

(54) SKIN-PRINT FLUORESCENCE ANALYSIS METHOD AND APPARATUS

(71) Applicant: INTELLIGENT FINGERPRINTING LIMITED, Cambridge, Cambridgeshire (GB)

(72) Inventors: Nicholas Earl, Cambridge (GB); Daniel Peterson Godfrey, Cambridge (GB); John Dunton, Cambridge (GB); Mark Hudson, Norwich (GB); David Russell, Norwich (GB)

(73) Assignee: INTELLIGENT FINGERPRINTING LIMITED, Cambridge (GB)

( * ) Notice: Subject to any disclaimer, the term of this patent is extended or adjusted under 35 U.S.C. 154(b) by 183 days.

(21) Appl. No.: 15/034,791

(22) PCT Filed: Nov. 7, 2014

(86) PCT No.: PCT/GB2014/053324
§ 371 (c)(1),
(2) Date: May 5, 2016

(87) PCT Pub. No.: WO2015/067961
PCT Pub. Date: May 14, 2015

(65) Prior Publication Data
US 2016/0274093 A1    Sep. 22, 2016

(30) Foreign Application Priority Data
Nov. 8, 2013 (GB) .................................. 1319757.9

(51) Int. Cl.
*G01N 35/00* (2006.01)
*G01N 33/53* (2006.01)
(Continued)

(52) U.S. Cl.
CPC ....... *G01N 33/5306* (2013.01); *A61B 5/0071* (2013.01); *A61B 5/1172* (2013.01);
(Continued)

(58) Field of Classification Search
CPC ......... G01N 33/5306; G01N 33/54366; G01N 1/312; G01N 21/00; G01N 2001/007;
(Continued)

(56) References Cited

U.S. PATENT DOCUMENTS

| 4,917,987 A | 4/1990 | Arndt et al. |
| 6,352,863 B1 | 3/2002 | Guirguis |

(Continued)

FOREIGN PATENT DOCUMENTS

| JP | S61154538 A | 7/1986 |
| JP | H02268744 A | 11/1990 |

(Continued)

OTHER PUBLICATIONS

Pompi Hazarika et al., "Advances in Fingerprint Analysis," Angewandte Chemie International Edition, vol. 51, No. 15, p. 3524-3531, Mar. 2012.

(Continued)

*Primary Examiner* — Dennis White
(74) *Attorney, Agent, or Firm* — Lando & Anastasi, LLP

(57) ABSTRACT

A method of analyzing a skin-print provided on a first surface of an optically transparent substrate. The method comprises the steps of exposing the skin-print on the first surface of the optically transparent substrate to one or more reagents selected to bind with one or more metabolites present in the skin-print; transmitting electromagnetic radiation onto the skin-print through the optically transparent substrate using a radiation source to thereby produce an optical signal of said one or more reagents and/or said one or more metabolites; and detecting an optical image of the (Continued)

optical signal through the optically transparent substrate using a sensor. Also a skin-print analysis apparatus and a reagent cartridge for use in carrying out the method.

9 Claims, 22 Drawing Sheets

(51) Int. Cl.
*A61B 5/1172* (2016.01)
*B01L 3/00* (2006.01)
*A61B 5/00* (2006.01)
*A61B 5/1455* (2006.01)
*A61B 5/1491* (2006.01)
*A61B 10/00* (2006.01)
*G01N 1/31* (2006.01)
*G01N 33/543* (2006.01)
*G01N 21/64* (2006.01)
*A61B 5/145* (2006.01)
*G01N 1/00* (2006.01)

(52) U.S. Cl.
CPC .......... *A61B 5/1455* (2013.01); *A61B 5/1491* (2013.01); *A61B 5/4845* (2013.01); *A61B 10/0064* (2013.01); *B01L 3/523* (2013.01); *B01L 3/527* (2013.01); *G01N 1/312* (2013.01); *G01N 21/645* (2013.01); *G01N 21/6428* (2013.01); *G01N 33/54366* (2013.01); *A61B 5/14517* (2013.01); *A61B 2010/0009* (2013.01); *A61B 2560/0406* (2013.01); *B01L 2200/025* (2013.01); *B01L 2200/026* (2013.01); *B01L 2200/16* (2013.01); *B01L 2300/069* (2013.01); *B01L 2300/0832* (2013.01); *B01L 2400/0478* (2013.01); *B01L 2400/084* (2013.01); *G01N 2001/007* (2013.01)

(58) Field of Classification Search
CPC .............. A61B 10/0064; A61B 5/4845; A61B 5/0071; A61B 5/1491; A61B 5/1455; A61B 5/1172; A61B 2010/0009; A61B 2560/0406; A61B 5/14517; B01L 3/523; B01L 3/527; B01L 2300/069; B01L 2200/16; B01L 2400/084; B01L 2300/0832; B01L 2200/025; B01L 2400/0478; B01L 2200/026

See application file for complete search history.

(56) References Cited

U.S. PATENT DOCUMENTS

| | | |
|---|---|---|
| 2004/0126281 A1 | 7/2004 | Morrison |
| 2005/0180891 A1 | 8/2005 | Webster et al. |
| 2009/0126625 A1* | 5/2009 | Salva Calcagno ... A61B 5/1172 118/31.5 |
| 2009/0230322 A1* | 9/2009 | Russell ................. B82Y 30/00 250/459.1 |
| 2012/0119906 A1 | 5/2012 | Kountotsis |
| 2012/0184025 A1 | 7/2012 | Kawata et al. |
| 2012/0214254 A1 | 8/2012 | Schmidt et al. |

FOREIGN PATENT DOCUMENTS

| | | | |
|---|---|---|---|
| JP | 2007182483 A | 7/2007 | |
| JP | 2013535998 A | 9/2013 | |
| WO | 02072264 A1 | 9/2002 | |
| WO | 2006115499 A1 | 11/2006 | |
| WO | 2007110605 A2 | 10/2007 | |
| WO | 2013111025 A1 | 8/2013 | |
| WO | WO-2013111025 A1 * | 8/2013 | ........ B01L 3/502715 |

OTHER PUBLICATIONS

European Communication Under Rule 71(3) EPC of the European Patent Office from corresponding EP Application Serial No. 14796873.9 dated Jul. 23, 2018.

European Examination Report of the European Patent Office from corresponding EP Application Serial No. 14796873.9 dated Mar. 22, 2018.

First Office Action of the State Intellectual Property Office of the People's Republic of China from corresponding CN Application Serial No. 201480072764.X dated Apr. 3, 2018.

Office Action of the Japanese Patent Office from corresponding JP Application Serial No. 2016-526899 dated Aug. 7, 2018.

\* cited by examiner

SKIN-PRINT FLUORESCENCE ANALYSIS METHOD AND APPARATUS

CROSS-REFERENCE TO RELATED APPLICATIONS

This application is a U.S. national phase application and claims the benefit of priority under 35 U.S.C. § 371 of International (PCT) Patent Application Serial No. PCT/GB2014/053324, titled SKIN-PRINT FLUORESCENCE ANALYSIS METHOD AND APPARATUS and filed on Nov. 7, 2014, which in turn claims priority to Serial No. GB1319757.9 filed on Nov. 8, 2013.

BACKGROUND

An impression left by the friction ridges of human skin, such as the skin of a human finger, contains information regarding the identity of the human. It is widely known that the appearance of the impression of the human finger, known as a fingerprint, is unique to each human and may be used to confirm the identity of the human. The appearance of the impression of the skin of other human body parts may also be unique to each human and so may also be used to confirm the identity of the human. Such impressions of human skin, when not specific to the skin of the human finger, may be called skin-prints.

In addition to the appearance of the impression left by human skin, the impression may contain chemical species which themselves may be detected in order to obtain further information.

For example, when a human intakes a substance (e.g. by ingestion, inhalation or injection) the substance may be metabolised by the human body giving rise to secondary chemicals known as metabolites. The presence of a particular metabolite can be indicative of a specific intake substance. These metabolites may be present in sweat and, as such, may be left behind in the skin-print, e.g. a skin-print. Detection of such metabolites in a skin-print can be used as a non-invasive method of testing for recent lifestyle activity such as (but not limited to) drug use. Importantly, the taking of a skin-print is much simpler than obtaining other body fluids such as blood, saliva and urine, and is more feasible in a wider range of situations.

Not only this but since the appearance of the skin-print itself provides confirmation of the identity of the person providing the skin-print, there can be greater certainty that the metabolites in the skin-print are associated with the individual. This is because substitution of a skin-print, particularly a fingerprint, is immediately identifiable from appearance whereas substitution of, for example, urine, is not immediately identifiable from appearance. As such, testing for metabolites in a skin-print provides a direct link between the metabolite and the identity of the human providing the skin-print.

STATEMENTS OF INVENTION

Against this background, there is provided a method of analysing a skin-print provided on a first surface of an optically transparent substrate, the method comprising the steps of:
  exposing the skin-print on the first surface of the optically transparent substrate to one or more reagents selected to bind with one or more metabolites present in the skin-print;
  illuminating the skin-print through the optically transparent substrate using a radiation source to thereby produce an optical signal of said one or more reagents and/or said one or more metabolites;
  detecting an optical image of the optical signal through the optically transparent substrate using a sensor.

In a further aspect, there is provided a skin-print analysis apparatus comprising:
  a reagent supply assembly for providing one or more reagents selected to bind with one or more metabolites present in a skin-print;
  a holder for retaining an optically transparent substrate bearing a skin-print in fluid communication with the reagent source;
  a radiation source selected for producing an optical signal from said one or more reagents and/or said one or more metabolites; and
  a sensor for detecting an optical image of the optical signal;
  wherein the radiation source is positioned to transmit electromagnetic radiation onto the skin-print through the optically transparent substrate and the sensor is positioned to detect the image through the optically transparent substrate.

In a still further aspect, there is provided a reagent cartridge for dispensing fluid into contact with a test substrate, the reagent cartridge comprising:
  a body comprising a surface having an open-topped recess, the body further comprising a plurality of fluid reservoirs, each fluid reservoir being associated with a dispensing port in the body to provide fluid communication between said reservoir and the surface; and
  an actuator associated with each fluid reservoir of the plurality of fluid reservoirs, each actuator being configured to dispense from the associated dispensing port some or all of a fluid which may be present in the associated fluid reservoir,
  wherein the surface is configured to receive a test substrate to seal the open-topped recess so as to form a fluid-tight flow path incorporating at least one of the dispensing ports and the recess.

It may be that, in use, the optically transparent substrate is retained within a skin-print capture and transport unit and the holder is configured to receive said skin-print capture and transport unit. In this way, it is possible to protect the skin-print substrate within the skin-print capture and transport unit once a skin-print has been received and then transport the skin-print capture to the skin-print analysis apparatus which both opens the skin-print capture and transport unit to access the substrate and analyses the skin-print present on the substrate.

While these aspects of the invention are particularly appropriate to analysis of fingerprints, they may be used in relation to any skin-prints such as, but not limited to, ear prints, toe prints and palm prints. Analysis of all such skin-prints falls within the scope of the present disclosure.

BRIEF DESCRIPTION OF THE DRAWINGS

Specific embodiments of the invention will now be described, by way of example only, with reference to the accompanying drawings in which.

SPECIFIC DESCRIPTION

Figure 1:
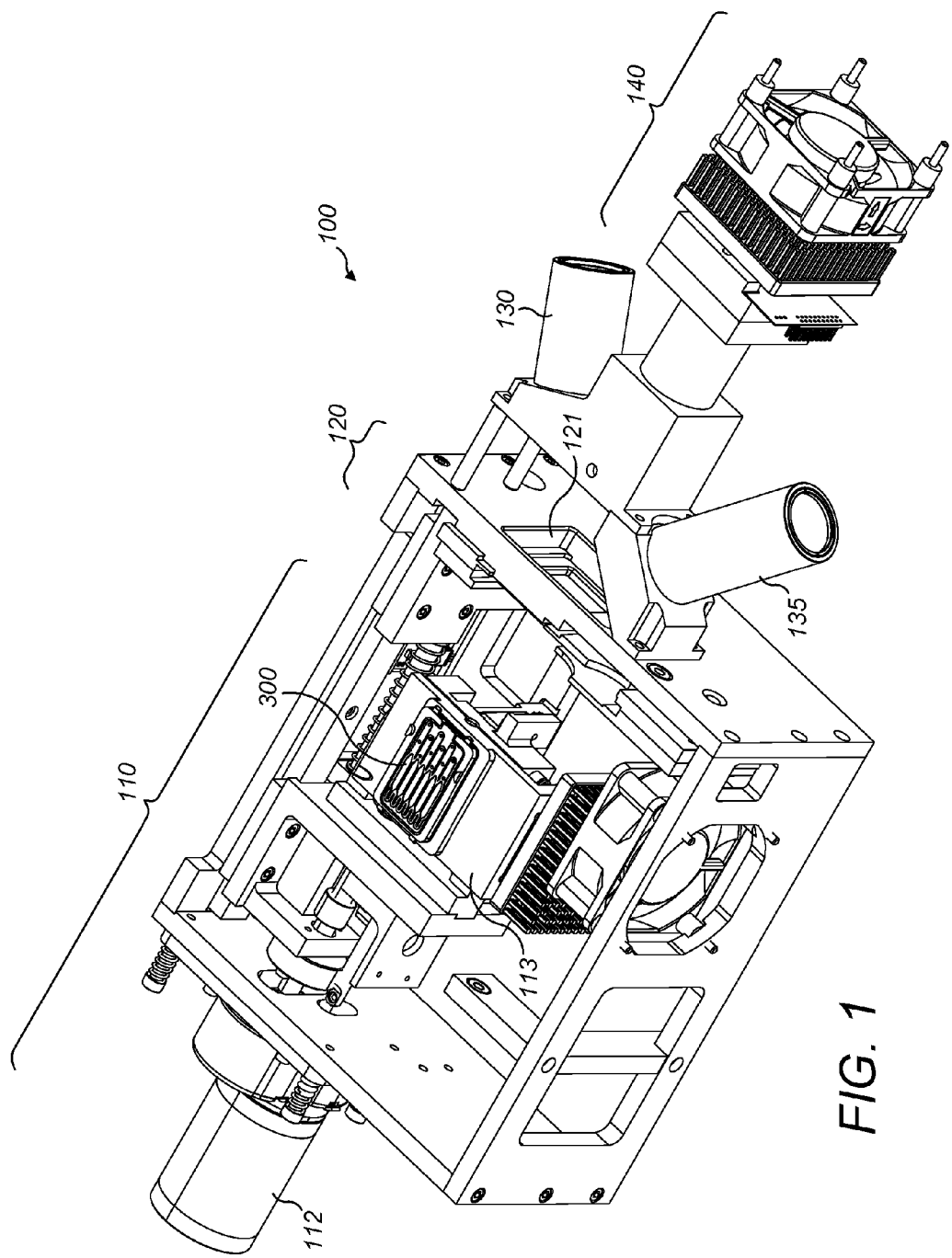
FIG. 1 shows a preferred embodiment of a skin-print analysis apparatus in an initial configuration.
Figure 2:
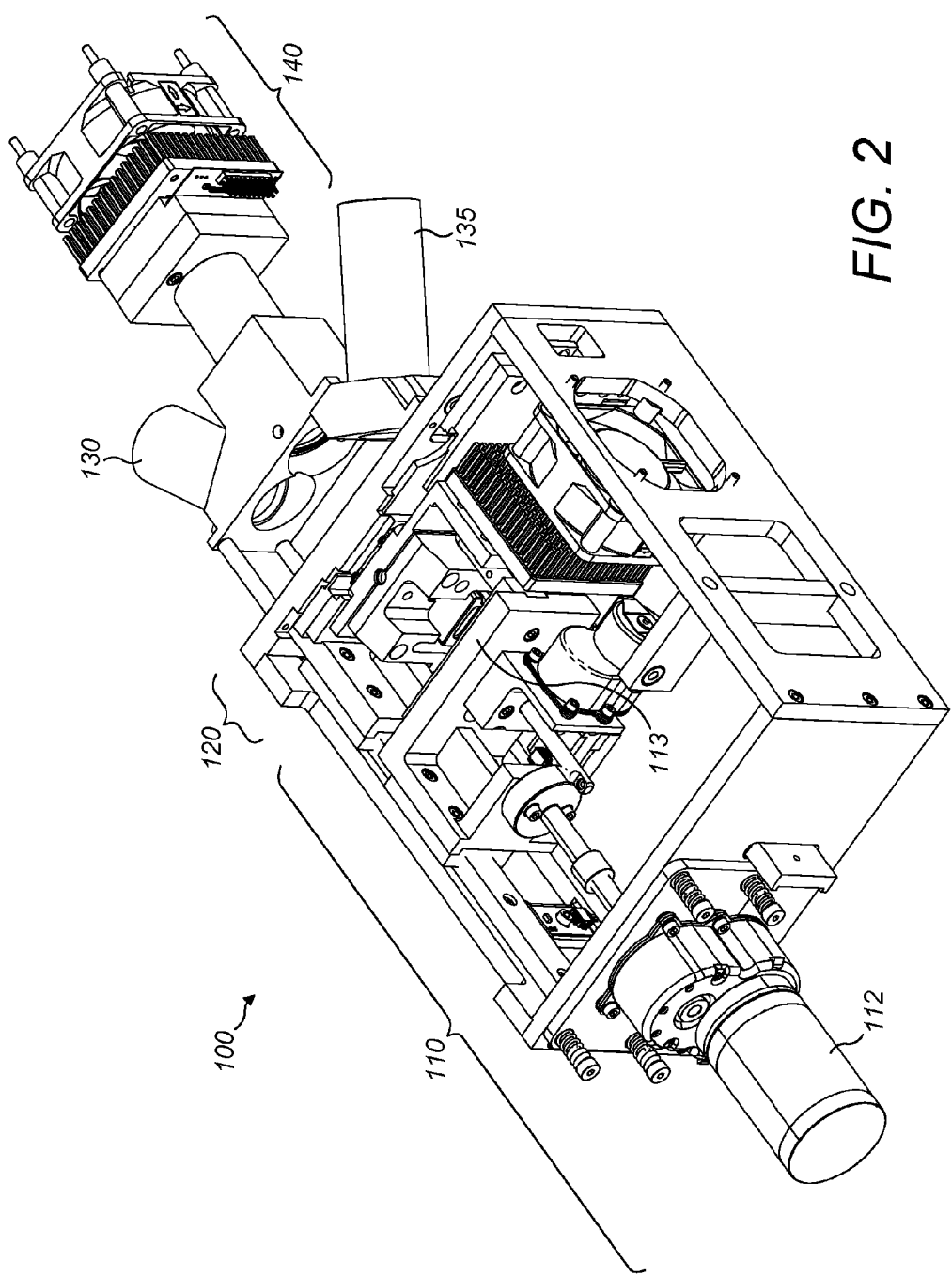
FIG. 2 shows the skin-print analysis apparatus of FIG. 1 in an analysing configuration.

A preferred embodiment of a skin-print analysis apparatus 100 is shown in FIGS. 1 and 2.

Figure 16:
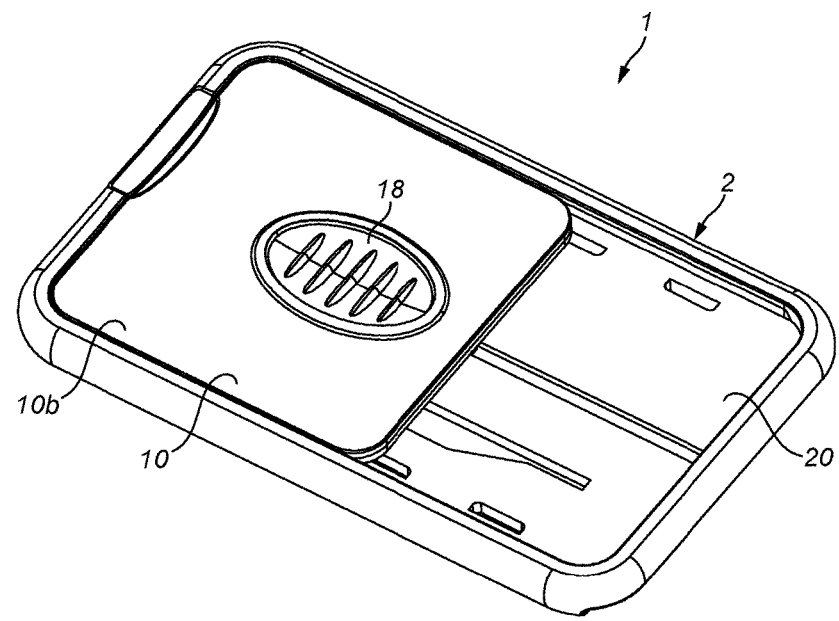
FIG. 16 shows a front view of skin-print capture and storage unit for use with the second embodiment of the skin-print analysis apparatus.

This preferred embodiment is configured for analysing a substrate 200 which is mounted within a skin-print capture and transport unit 1 (as shown in FIG. 16). Consequently, some of the features of the preferred embodiment of the skin-print analysis apparatus 100 relate specifically to its compatibility for use with the said skin-print capture and transport unit 1. As the skilled person will readily appreciate, the invention is not limited to a skin-print analysis apparatus 100 configured for use with the particular skin-print capture and transport unit 1. Other embodiments of the invention operate equally well with substrates housed in other units and substrates which are not otherwise housed. Therefore, while the following description is specific to use of the invention with a skin-print capture and transport unit 1, to the extent that features are specific to the skin-print capture and transport unit 1, this should not be considered limiting on the scope of the claims.

In order to assist in explaining those features of the preferred skin-print analysis apparatus 100 which render it suitable for use with a skin-print capture and transport unit 1, an explanation of the skin-print capture and transport unit 1 now follows.

Skin-Print Capture and Transport Unit

The optically transparent substrate 200 is enclosed within a housing 2 of the skin-print capture and transport unit 1, as shown in FIG. 16.

Figure 3:
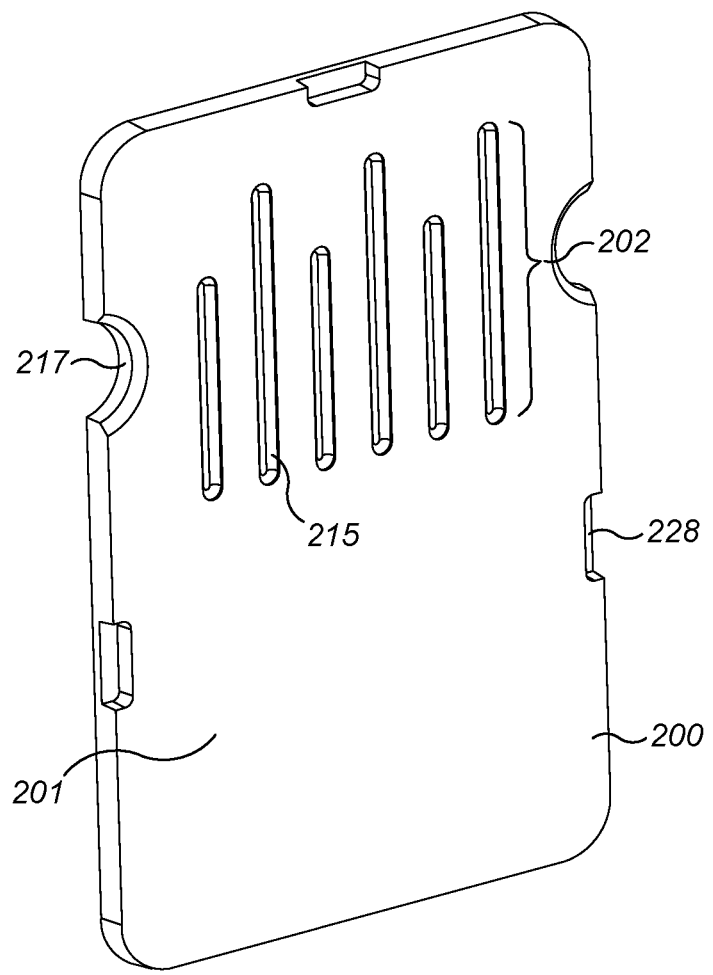
FIG. 3 shows a substrate for receipt of a skin-print suitable for analysis by the skin-print analysis apparatus of FIGS. 1 and 2.

The optically transparent substrate 200 (as shown in FIG. 3) may comprise a sample receiving zone 201 for receiving a skin-print and a fluid transmission zone 202 comprising one or more grooves 215 for directing fluid towards the sample receiving zone 201. The substrate 200 is described in more detail below.

Figure 17:
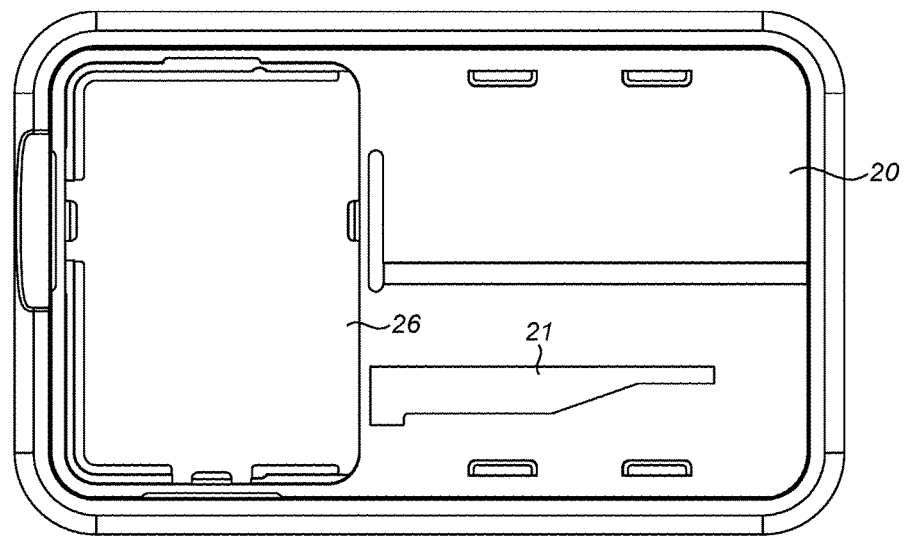
FIG. 17 shows a top side of a frame of the skin-print capture and storage unit of FIG. 16.
Figure 21:
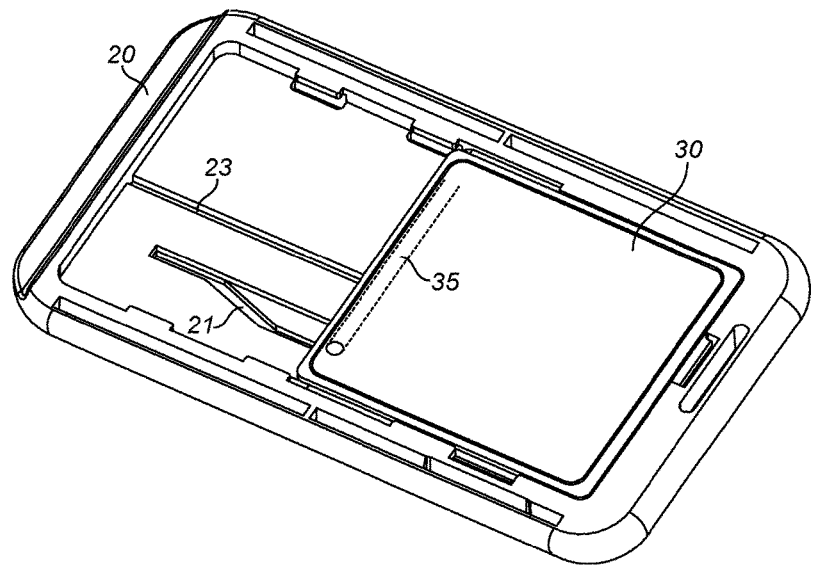
FIG. 21 shows a rear view of skin-print capture and storage unit of FIG. 16.
Figure 22:
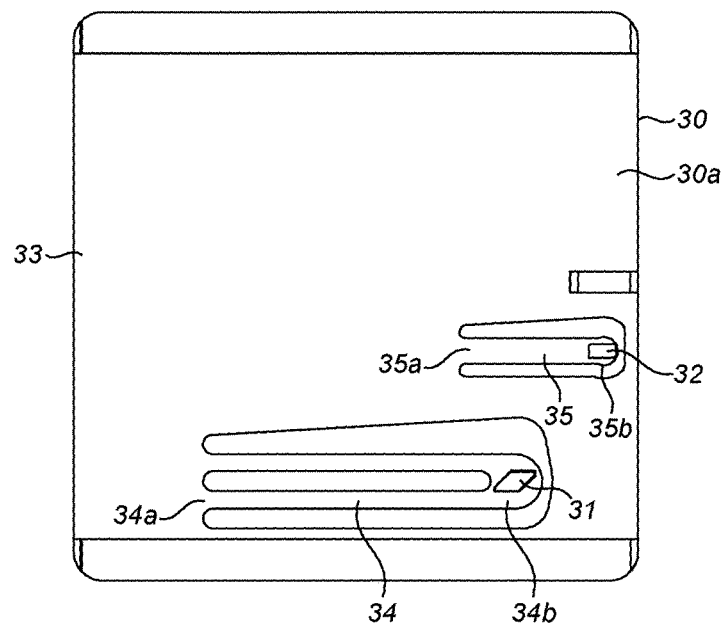
FIG. 22 shows an inside view of a rear shutter of the skin-print capture and storage unit of FIG. 16.
Figure 23:
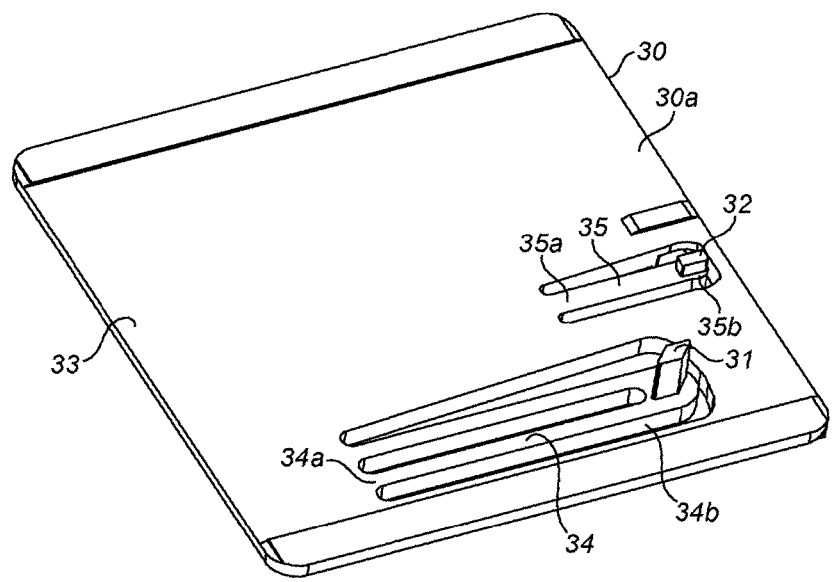
FIG. 23 shows a perspective inside view of a rear shutter of the skin-print capture and storage unit of FIG. 16.
Figure 24:
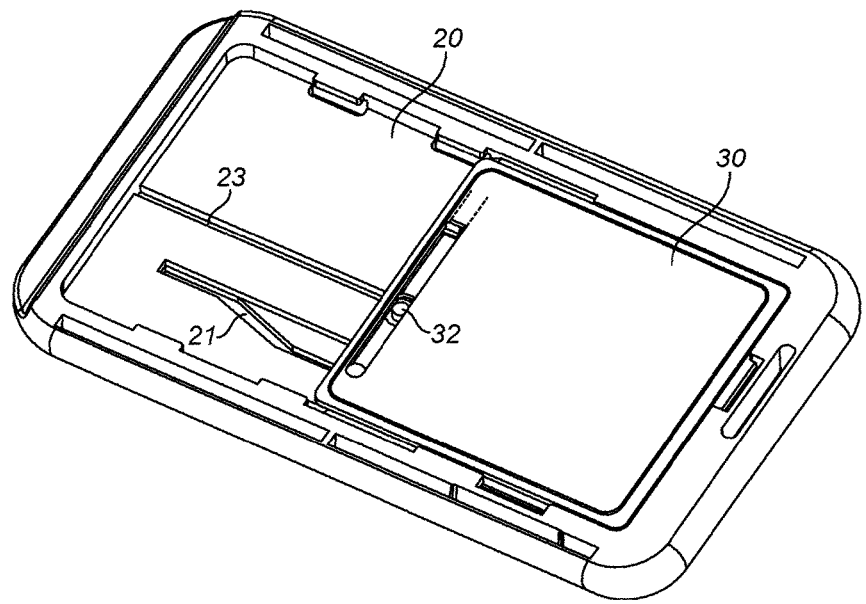
FIG. 24 shows a rear view of the skin-print capture and storage unit of FIG. 16 wherein a frangible element of the rear cover is broken to show access to a pin.

The housing 2 of the skin-print capture and transport unit 1 acts to protect the substrate except when it is necessary for it to be exposed (in particular, for receiving a skin-print and for analysis). The housing 2 comprises a frame 20 with a substrate receiving portion 26, best shown in FIG. 17. The housing 2 also comprises a front shutter 10 (best shown in FIG. 16) and a rear shutter 30 (best shown in FIG. 21). The front shutter 10 comprises an inside 10a that faces inwardly towards the substrate and an outside 10b which faces outwardly. The front shutter 10 may further comprise a thumb grip 18 on the outside 10b of the front shutter. The rear shutter 30 comprises an inside 30a that faces inwardly towards the substrate and an outside 30b which faces outwardly.

The front shutter 10 is movable with respect to the frame 20 from a first closed position (shown in FIG. 16) in which the front surface of the substrate is covered by the front shutter 10 to a first open position in which the front surface of the substrate is exposed, in particular for receipt of a skin-print.

The front shutter 10 is also movable with respect to the frame 20 from the first open position to a second closed position in which the front surface of the substrate is covered by the front shutter 10.

Figure 19:
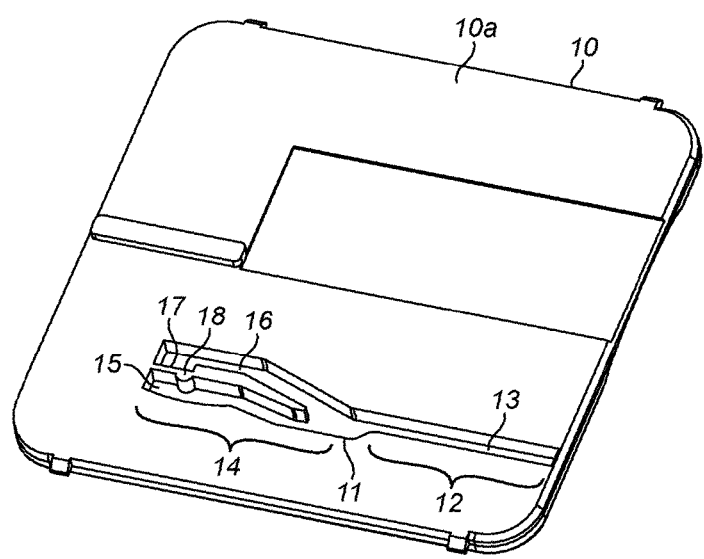
FIG. 19 shows an inside of the front shutter of the skin-print capture and storage unit of FIG. 16.
Figure 20:
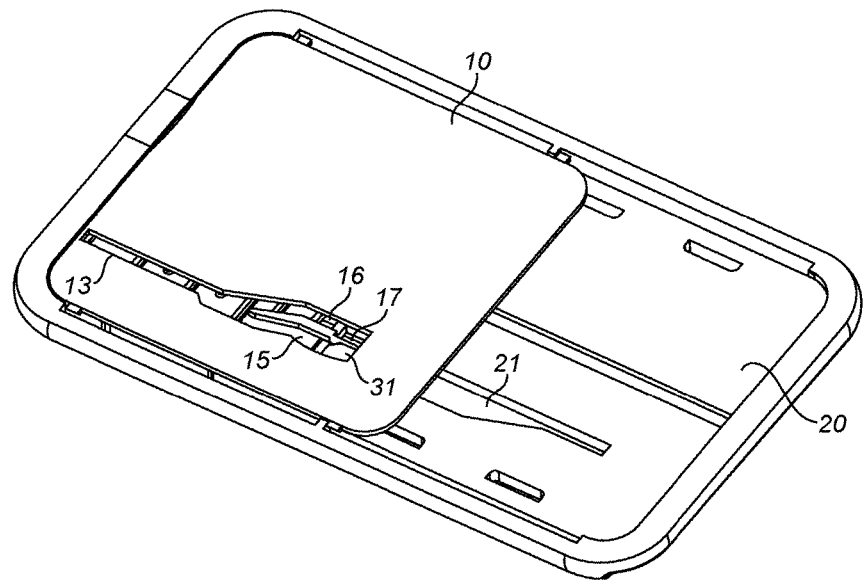
FIG. 20 shows a section through the front shutter of FIGS. 18 and 19 in situ of the skin-print capture and storage unit of FIG. 16.

The inside 10a of the front shutter 10 comprises a bifurcated channel arrangement 11, best seen in FIG. 19. The bifurcated channel arrangement 11 comprises a first part 12 comprising a common channel 13 and a second part 14 comprising a primary channel 15 and a secondary channel 16, the primary channel 15 and the secondary channel 16 being substantially parallel. The primary channel comprises a protrusion 18 and the secondary channel comprises a first detent 17.

The rear shutter 30 comprises a body 33, a first elongate member 34 and a second elongate member 35. The first elongate member 34 has a proximal end 34*a* which extends from the body 33 and a distal end 34*b*. This allows some flexibility of the distal end 34*b* with respect to the body 33. A first pin 31 is located at the distal end 34*b* of the first elongate member 34 and extends from the inside face 30*a* of the rear shutter 30. The first elongate member 34 comprises two parallel beams which act to increase flexibility of the distal end 34*b* of the elongate member 34 with respect to the body.

Figure 26:
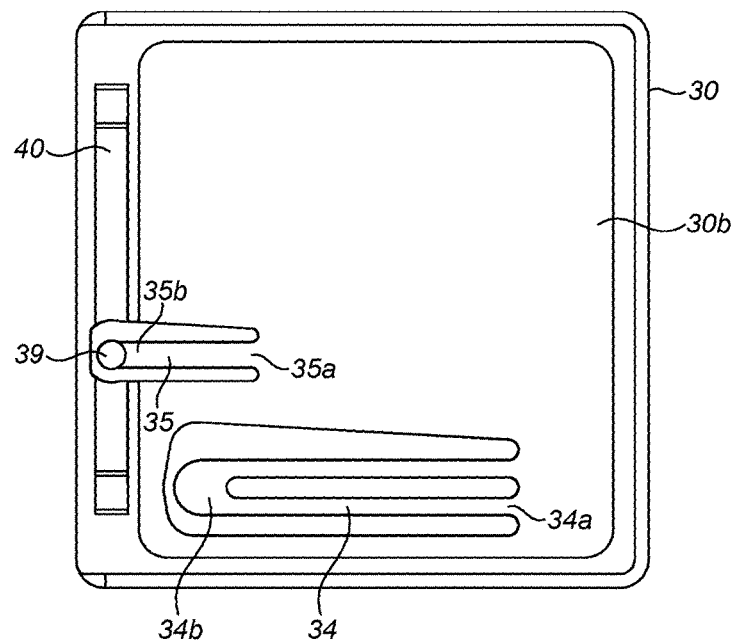
FIG. 26 shows an outside view of a rear shutter of the skin-print capture and storage unit of FIG. 16 with a cover of the rear shutter removed.

The second elongate member 35 has a proximal end 35*a* which extends from the body 33 and a distal end 35*b*. This allows some flexibility of the distal end 35*b* with respect to the body 33. A second pin 32 is located at the distal end 35*b* of the second elongate member 35 and extends from the inside face 30*a* of the rear shutter 30. A third pin 39 is located at the distal end 35*b* of the second elongate member 35 and extends from the outside face 30*b* of the rear shutter 30 (as shown in FIG. 26).

Figure 25:
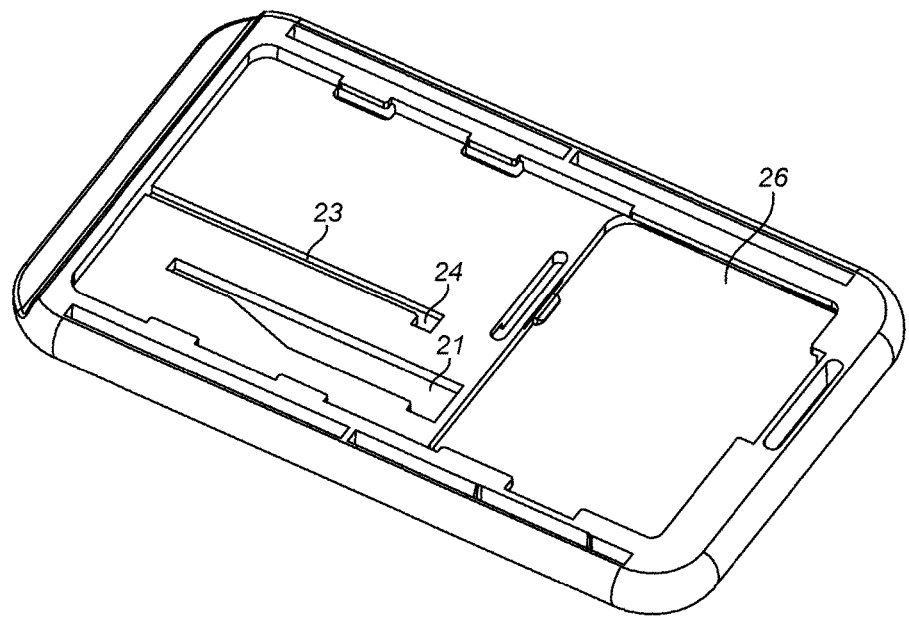
FIG. 25 shows a bottom side of the frame of the skin-print capture and storage unit of FIG. 16.

The first pin 31 has a diamond-shaped cross-section, the second pin 32 has a rectangular-shaped cross-section and the third pin 33 has a circular cross-section. The first pin 31 is longer than the second pin 32. The first pin 31 is arranged to protrude through an aperture 21 in the frame 20 (best shown in FIG. 25) and is retained within the bifurcated channel arrangement 11 of the front shutter 10. The aperture 21 is shaped so that it does not act to prevent movement of the pin within the bifurcated channel arrangement 11 of the front shutter 10.

Figure 18:
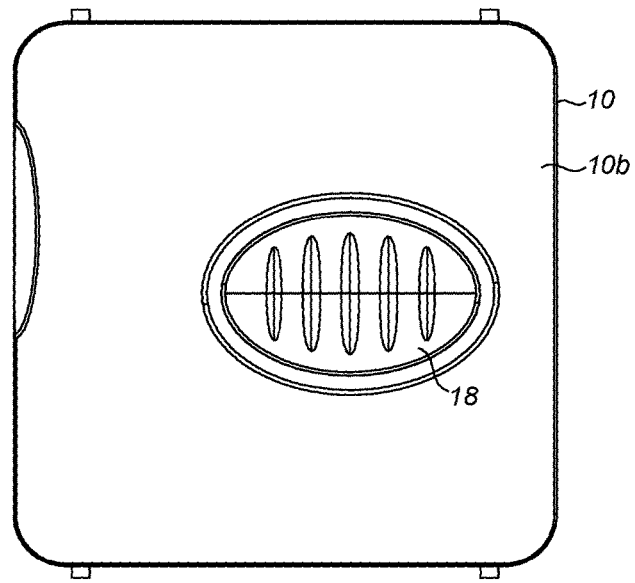
FIG. 18 shows an outside of a front shutter of the of the skin-print capture and storage unit of FIG. 16.

In the first closed position of the front shutter (FIG. 16, FIG. 18), the first pin 31 is located at or towards an end of the primary channel 15 that is furthest from the common channel 13.

Sliding the front shutter 10 from the first closed position into the first open position causes the first pin 31 to pass along the primary channel 15 into the common channel 13. The protrusion 18 in the primary channel provides resistance which must be overcome in order for the front shutter to move from the first closed position into the first open position. The protrusion has a smooth cross-sectional shape which results in a gradual reduction in width of the primary channel 15. Resistance must be overcome in order for the diamond-shaped first pin 31 to pass the protrusion. The purpose of the resistance is to avoid the front shutter moving unintentionally from the first closed position into the first open position. For example, it avoids the front shutter moving from the first closed position to the first open position merely under gravity which might otherwise happen in the event that the skin-print capture and transport unit 1 is positioned so that the common channel 13 is below the primary channel 15.

In the first open position of the front shutter 10, the first pin 31 is located at or towards an end of the common channel 13 which is furthest from the primary and secondary channels 15, 16.

Sliding the front shutter, again using the thumb grip 18, from the first open position into the second closed position causes the first pin 31 to pass along the common channel 13 into the secondary channel 16. The front shutter 10 is prevented from returning to the first closed position since the first pin is prevented from travelling into the primary channel 15 by virtue of one or more kinks in the primary channel 15 and/or the secondary channel 16. Alternatively, or in addition, the first pin 31 may be prevented from travelling into the primary channel 15 by virtue of a biasing effect on the first pin 31. In the specific embodiment illustrated herein, an axis of the primary channel 15 diverges away from an axis of the common channel 13 as the primary channel 15 approaches the common channel 13. Conversely, an axis of the secondary channel 16 converges towards the axis of the common channel 13 as the secondary channel 16 approaches the common channel 13.

In this way, as the first pin moves down the primary channel 15 towards the common channel 13, it is increasingly biased transversely of the axis of the primary channel 15. Once the first pin 31 moves into the common channel 13 it falls back to an unbiased transverse position.

As the first pin moves down the common channel 13 towards the secondary channel 16, the first pin 31 is unbiased and, as such, as it moves axially there is no transverse biasing which would be necessary to cause it to pass into the primary channel 15. This results in the first pin 31 passing into the secondary channel 16. As the first pin moves down the secondary channel 16 away from the common channel 13, the axis of the secondary channel 16 diverges from the axis of the common channel which means that the first pin 31 is increasingly transversely biased.

In the second closed position, the first pin 31 is received into a first detent 17 which is located at or towards an end of the secondary channel 16 furthest from the common channel 13. Receipt of the first pin 31 into the first detent 17 is caused by the transverse biasing on the pin. Once the pin moves transversely to be received into the first detent 17, the transverse biasing is much reduced or eliminated.

In the second closed position, with the first pin 31 received into the first detent 17, the diamond shaped cross-sectional shape of the first pin 31 combined with the step-shaped first detent 17 and the absence of biasing on the first pin 31 mean that the first pin 31 is not removable from the first detent 17. As such, the front shutter 10 is prevented from moving from the second closed position into the first open position.

The rear shutter 30 is movable with respect to the frame from a closed position in which the rear surface of the substrate is covered by the rear shutter 30 to an open position in which the rear surface of the substrate is exposed for analysis of the appearance of the skin-print through the transparent substrate.

The frame 20 comprises an elongate groove 23 including a second detent 24. In the closed position of the rear shutter 30 the second pin 32 of the rear shutter is retained in the second detent 24.

The rear shutter 30 comprises a cover having a frangible element 35 positioned such that, in the closed position of the rear shutter 30, the frangible element 35 is proximate to the second detent 24 in the frame 20 such that the third pin 39 is accessible only by breaking, removing or otherwise irreversibly damaging the frangible element 35. As such, the frangible element 35 provides evidence of whether or not the third pin 39 has been accessed. In the event that the frangible element 35 is damaged there is evidence that the third pin 39 is accessible and, as such, there can be no certainty that the substrate is uncontaminated. The frangible element 35 therefore acts as a tamper evident feature of the skin-print capture and transport unit 1.

Breaking the frangible element 35 allows access to the third pin 39. Once accessible, the third pin 39 can be moved transversely which causes the distal end 35*b* of the second elongate member 35 also to move transversely. This has the further effect of causing the second pin 32 to move transversely which allows the second pin 32 to be removed from the second detent 24. Consequently, the second pin 32 may slide along the groove 23 such that the rear shutter 30 is openable with respect to the frame 20 into the open position of the rear shutter 30. Beneath the frangible element 35 there is an elongate slot 40 perpendicular to the elongate grove 23. An elongate actuator (see, for example, actuator 123 in FIG. 12) may be received into the elongate slot 40 once the tamper evident feature is triggered. Movement of the elongate actuator in a direction parallel to the direction of the elongate groove 23 causes the third pin 39 to slide along the elongate groove 23 in the sliding direction.

Since the first pin 31 is fixedly attached to the rear shutter 30 and, in the second closed position of the front shutter 10, the first pin 31 is received into the first detent 17 which prevents movement of the first pin 31 relative to the front shutter 10, so the rear shutter 30 is fixedly connected to the front shutter 10.

As a consequence, in the event that the second pin 32 is removed from the second detent 24 and passes along the groove 23 in order that the rear shutter 30 opens, at the same time the front shutter 10 also opens by moving from the second closed position to a second open position.

Figure 27:
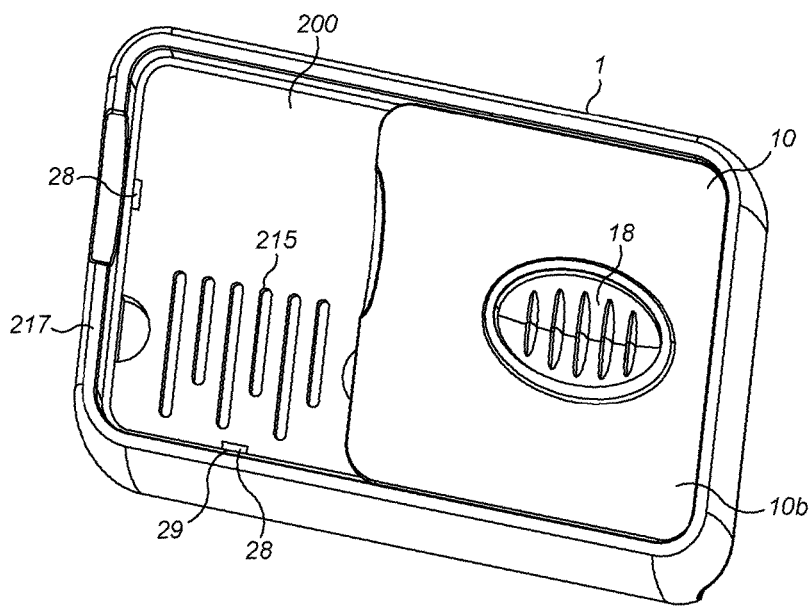
FIG. 27 shows a perspective view of the skin-print capture and storage unit of FIG. 16 with the substrate of FIG. 3 installed therein.

The skin-print capture and transport unit 1 further comprises a plurality of lugs 28 on an inner surface of the frame 20 adjacent the substrate receiving portion 26 which are configured to be received into corresponding detents 228 in the substrate, as best shown in FIG. 27. In this way, the substrate 200 may be snap-fitted to the skin-print capture and transport unit 1 such that removal of the substrate 200 from the skin-print capture and transport unit 1 is inhibited.

Figure 4:
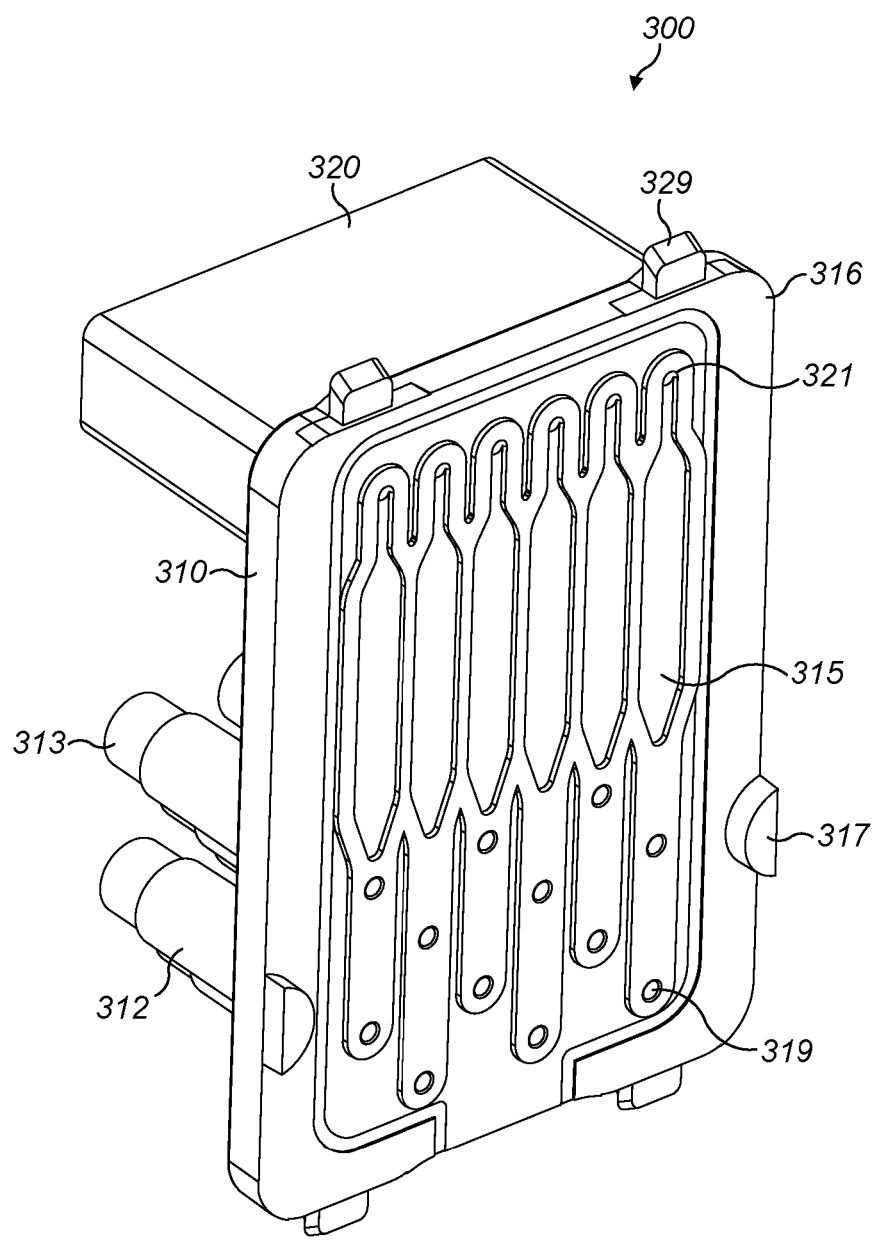
FIG. 4 shows a reagent cartridge of the skin-print analysis apparatus of FIGS. 1 and 2.

The skin-print capture and transport unit 1 further comprises a plurality of detents 29 in the inner surface of the frame 20 of the skin-print capture and transport unit 1 adjacent the substrate receiving portion 26, as shown in FIG. 27. The detents 29 are configured to receive a plurality of lugs 329 on an outer facing edge of the reagent cartridge 300, as shown in FIG. 4. In this way, the reagent cartridge 300 may be snap-fitted to the skin-print capture and transport unit 1 in a position where the substrate is flush with a sealing surface 316 of the reagent cartridge 300. The snap-fitting is such that removal of the reagent cartridge 300 from the skin-print capture and transport unit 1 is inhibited.

Since, as described, both the substrate 200 and the reagent cartridge 300 may be inhibited from being removed from the skin-print capture and transport unit 1, effectively, in this way the reagent cartridge 300 is inhibited from being removed from the substrate 200.

Use of the skin-print capture and transport unit 1 for obtaining a skin-print is discussed below, at the end of the description.

Skin-Print Analysis Apparatus of the Preferred Embodiment

The skin-print analysis apparatus 100 of the preferred embodiment (shown in FIGS. 1 and 2) comprises a reagent supply assembly 110, a holder 120, an excitation radiation source 130 an illumination radiation source 135 and a sensor 140. The skin-print apparatus 100 may further comprise one or more Peltier heat transfer devices to alter temperatures within the device to maximise performance, as discussed further below.

Figure 5:
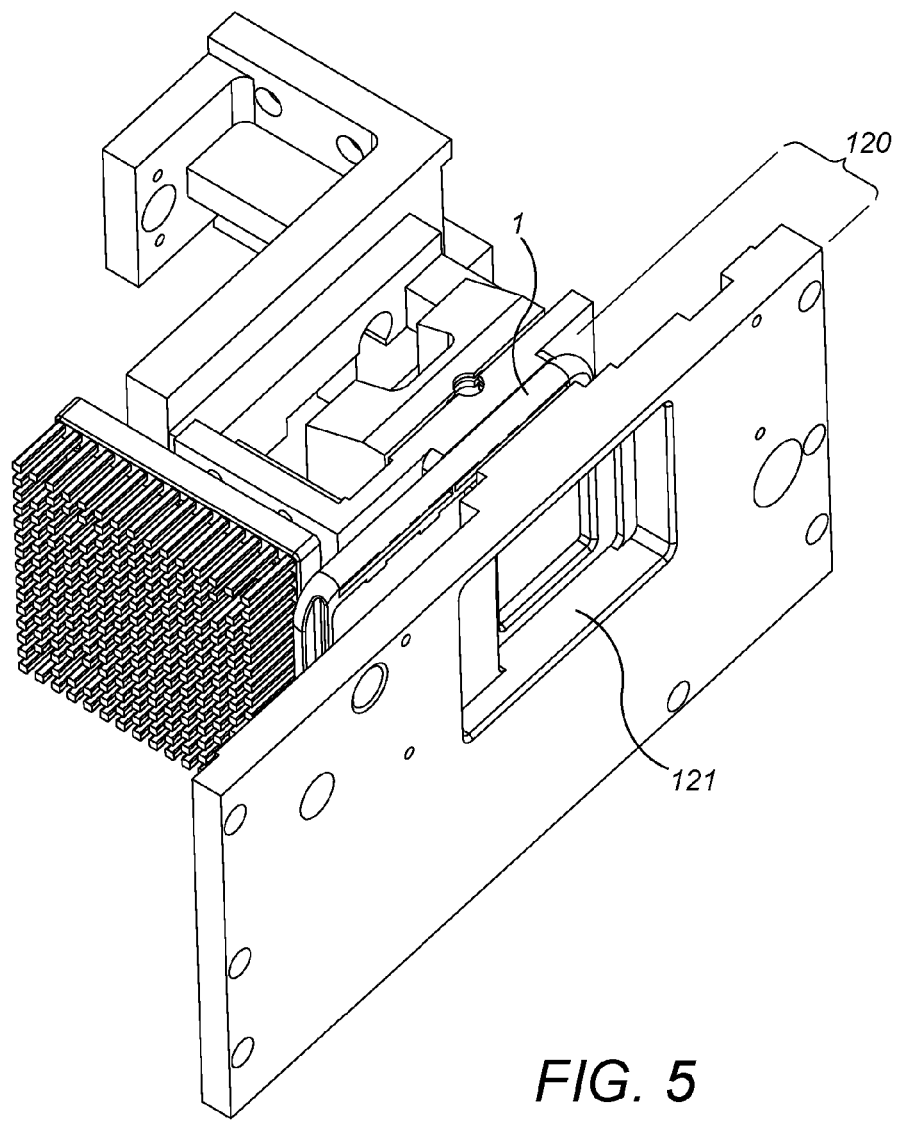
FIG. 5 shows a holder and part of a reagent supply assembly of the skin-print analysis apparatus of FIGS. 1 and 2.
Figure 6:
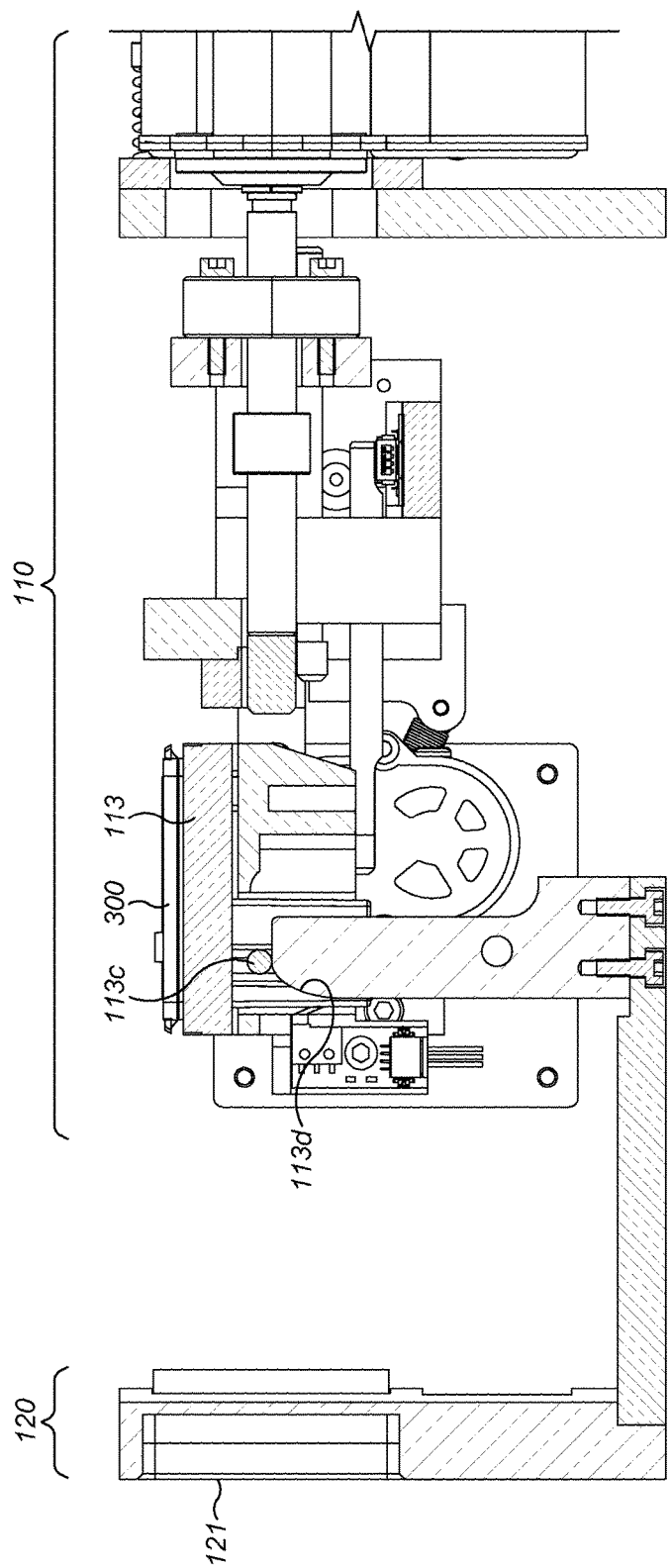
FIG. 6 shows the reagent supply assembly of the skin-print analysis apparatus of FIGS. 1 and 2 in an initial configuration in which the reagent cartridge is receivable from above.

The holder 120 comprises an aperture 121 which includes a window, preferably of quartz, that allows the passage of electromagnetic radiation. The holder 120 is configured to receive the skin-print capture and transport unit 1 which includes the optically transparent substrate 200 such that the optically transparent substrate 200 is positioned adjacent and parallel to the aperture 121 (as shown in FIG. 5). The optically transparent substrate 200 has a front surface onto which a skin-print may previously have been received and a rear surface opposite the front surface. The front surface is oriented to face towards the reagent supply assembly 110 and away from the excitation radiation source 130, the illumination radiation source 135 and the sensor 140.

The reagent supply assembly 110 is configured to receive a reagent cartridge 300, a preferred embodiment of which is described in more detail below.

The reagent supply assembly 110 comprises a movable reagent cartridge mount 113 for receiving, aligning and moving the reagent cartridge 300. The movable reagent cartridge mount 113 is shown in various positions in FIGS. 6 to 9.

Figure 14:
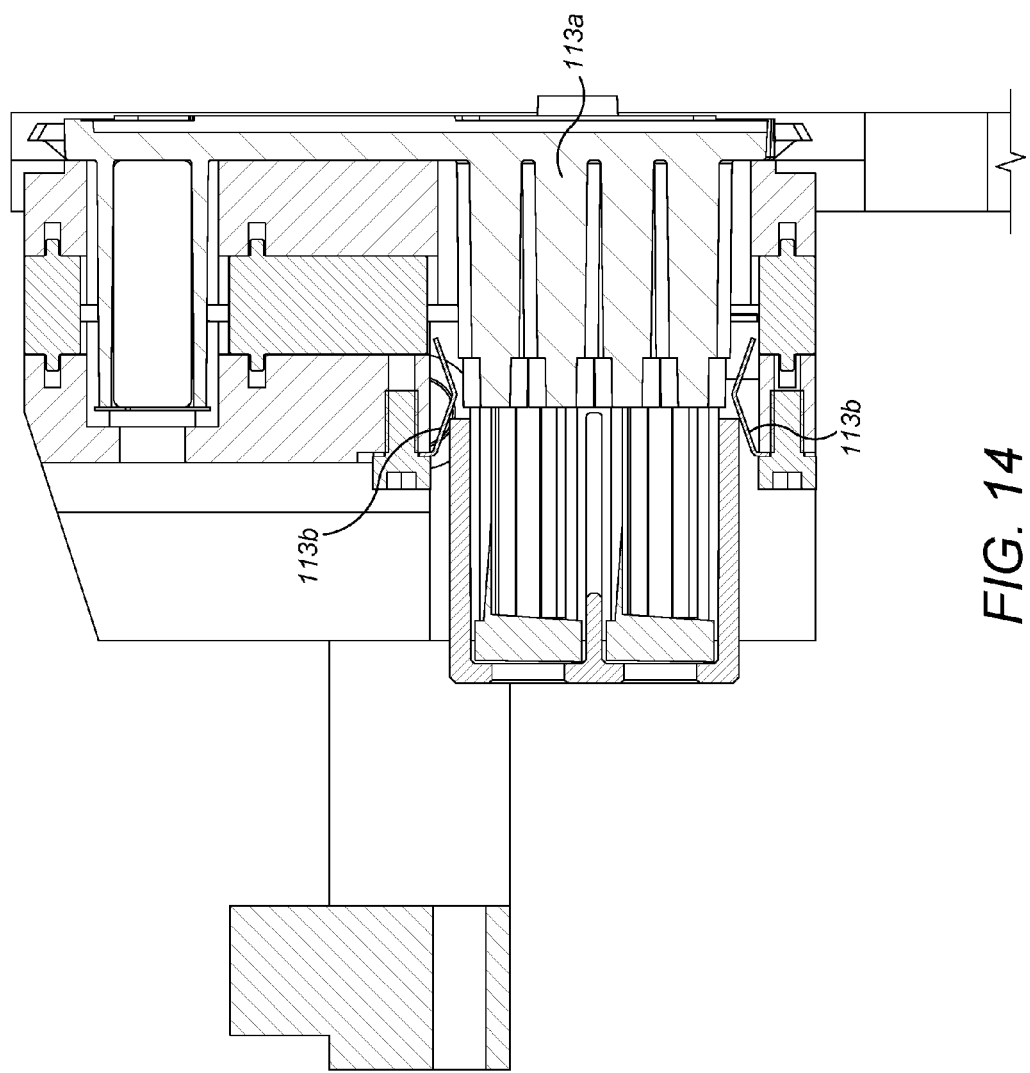
FIG. 14 shows the reagent supply assembly when viewed from above.

The movable reagent cartridge mount 113 comprises a cradle 113a into which the reagent cartridge 300 may be received. Specifically, when the skin-print analysis apparatus is in the initial configuration, shown in FIG. 6, the reagent cartridge is receivable from above. Retaining clips 113b, visible in FIG. 14, are mounted on the movable reagent cartridge mount 113 to provide resistance to the removal of the reagent cartridge 300.

Figure 8:
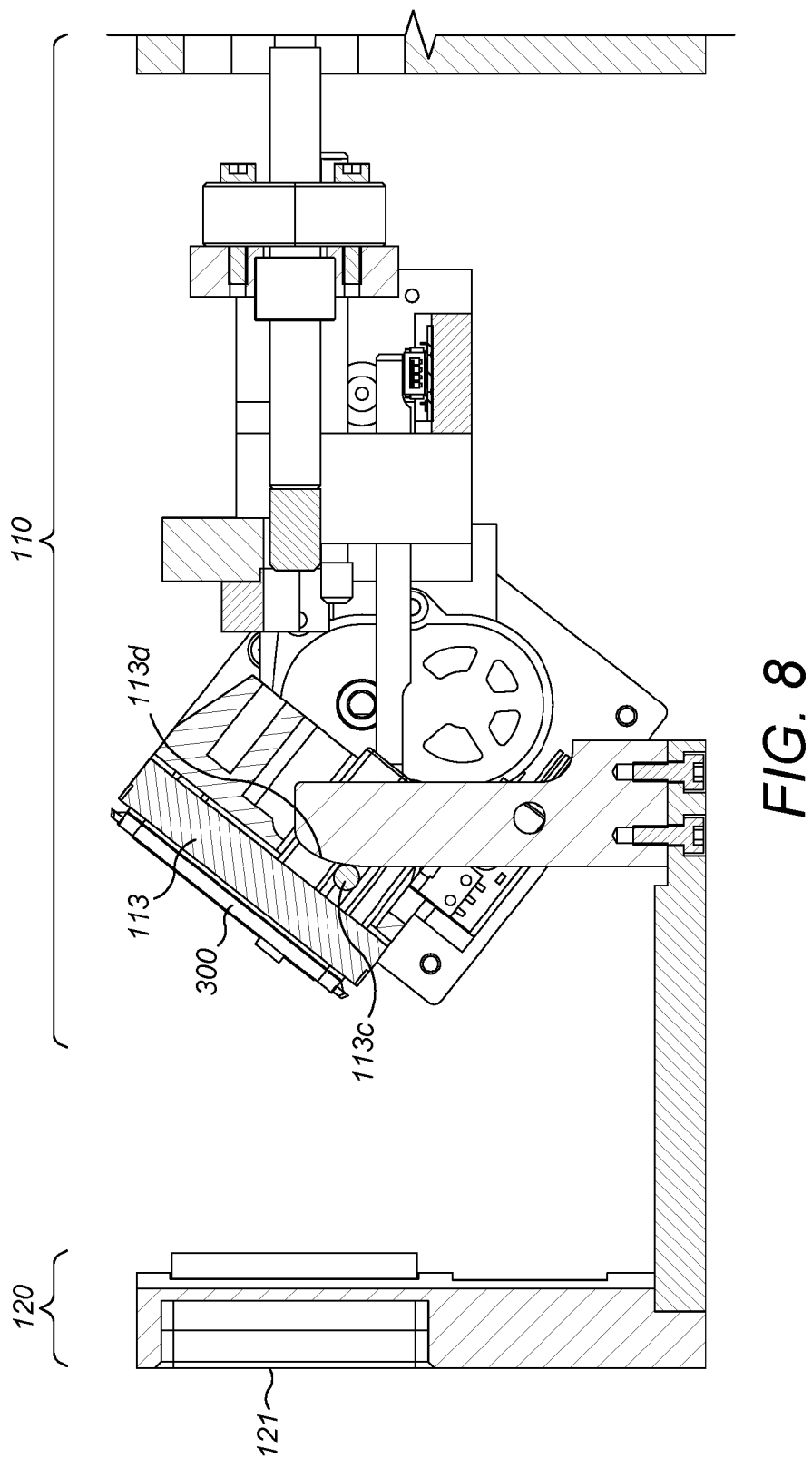
FIG. 8 shows a reagent supply assembly of a skin-print analysis apparatus in part-rotated configuration.
Figure 9:
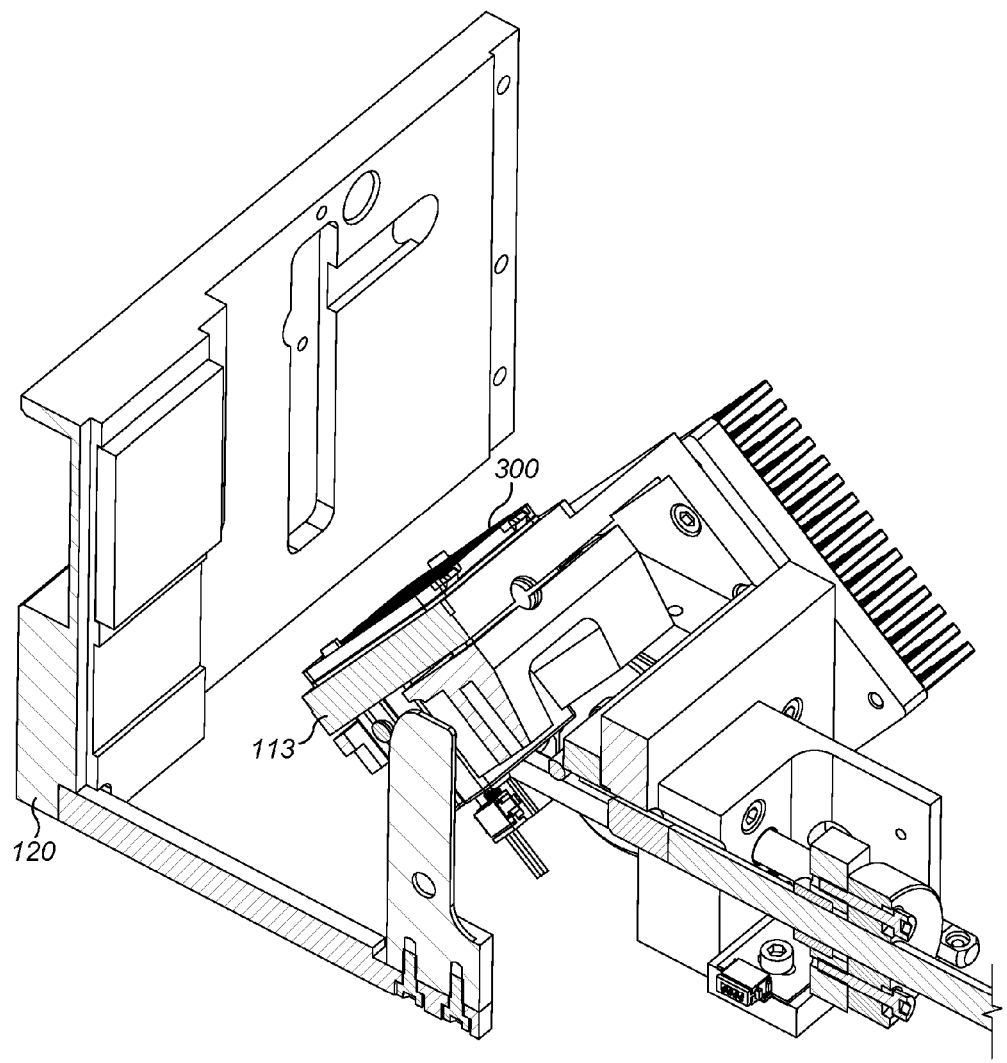
FIG. 9 is an isometric projection of that shown in FIG. 8.

The movable reagent cartridge mount 113 enables movement of the reagent cartridge 300 from an initial configuration distant from the aperture 121 (shown in FIGS. 1 and 6) to an intermediate configuration (shown in FIG. 7), in which the reagent cartridge 300 is rotated through 90°. FIGS. 8 and 9 show the reagent cartridge 300 in part rotated form. Subsequent to the rotation, the reagent cartridge mount 113 is movable laterally to an analysing configuration adjacent the aperture 121, as shown in FIG. 2.

Movement of the movable reagent cartridge mount 113 is effected by a stepper motor 112 located towards an end of the movable reagent cartridge mount 113 which is furthest from the holder 120. At a certain point in the travel of the stepper motor 112, translational movement of the stepper motor 112 is converted to rotational movement by virtue of a pin 113c mounted on the movable reagent cartridge mount 113 rolling over a curved ramp 113d fixedly attached to the reagent supply assembly 110.

The reagent supply assembly 110 comprises one or more actuator drivers (not shown) which are configured to engage with one or more actuator assemblies 330 of the reagent cartridge 300. The actuator assemblies 330 are configured to enable dispensing of fluid from one or more fluid reservoirs 312, 313 of the reagent cartridge 300 through one or more dispensing ports 319 of the reagent cartridge 300.

In the preferred embodiment there are two actuator drivers. One of the actuator drivers is configured to actuate a first actuator assembly 330a associated with a first set of reagent reservoirs 312 and the other of the actuator drivers is configured to actuate a second actuator assembly 330b associated with a second set of reagent reservoirs 313, as will be described further below in relation to the reagent cartridge 300.

The illumination radiation source 135 may, for example, be a white light LED. One particular example is an Avago™ ASMT-AGOO-NST00. This example has a 525 nm centre wavelength, 35 nm half power bandwidth which produces approximately 53 lm W$^{-1}$ at 300 mA and 3.5 V.

The excitation radiation source 130 may, for example, be a blue LED. One particular example is an Osram™ LV W5AM-JYKY-25. This example has a 495 nm dominant wavelength, 30 nm half power bandwidth which produces approximately 99 lm W$^{-1}$ at 100 mA and 3.2 V. Optionally, a filter may be located between the excitation radiation source 130 and the substrate 200, for example to pass a band of wavelengths to excite a fluorophor or to reject longer wavelength light.

The excitation radiation source 130 and the illumination radiation source 135 are both located on an opposite side of the aperture 121 in the holder 120 from the reagent supply assembly 110. As such, when a substrate is present in the holder 120, the excitation radiation source 130 and the illumination radiation source 135 are positioned to shine through the aperture 121, through the rear surface of the optically transparent substrate 200 onto the skin-print present on the front surface of the substrate.

The sensor 140 may, for example, be a low noise CCD (charge coupled device) array. One example would be a Aptina™ MT9M001 having a resolution of 1280×1024 with a 5.2 μm×5.2 μm monochrome sensor to give good dynamic range even in low light. A lens may be used to focus the light reaching the sensor 140. An example of a suitable lens may be an Edmund Optics™ 25 FL Megapixel Finite Conjugate Micro Video Lens. To enable longer exposure times a clock frequency of a chip controlling the CCD may be adjusted to provide an appropriate range of integration times. To obtain low background, the CCD array may be cooled using a Peltier cooler.

The sensor 140 is located on a same side of the aperture 121 as the excitation radiation source 130 and the illumination radiation source 135. The sensor 140 is parallel to the aperture and is located so as to receive electromagnetic radiation reflected by and emitted from the skin-print in contact with the reagent, the electromagnetic radiation having transmitted through the optically transparent substrate.

While in the illustrated embodiment, the illumination radiation source 135 and the excitation radiation source 130 are independent, in an alternative embodiment the illumination radiation source 135 and the excitation radiation source 130 may be a single source of radiation operated in two different modes dependent on the wavelength of radiation required (e.g. for illumination or for excitation).

Other features of the skin-print analysis apparatus 100 may include heat transfer devices by which heat can be transferred both to and from the substrate. These might be heat dissipaters such as a heat sink and/or a fan. Alternatively, these might be one or more peltier heat pump devices by which heat can be transferred both to and from the substrate. The purpose of heat transfer devices is to ensure optimum temperatures are present for the different process steps. For example, it may be that binding of the reagent to the substance occurs most efficiently at a first temperature (e.g. 37° C.) while fluorescent emission occurs most strongly at a second temperature (e.g. 15° C.). In addition, it may be that the sensor 140 is most sensitive when cooled to a third temperature (e.g. 10° C.). Various heat transfer devices may be included in the skin-print analysis apparatus 100 for these and other purposes.

Other additional features of the skin-print analysis apparatus 100 may include microswitches to detect the position of the moving parts by comparison with the expected positions. Furthermore, microswitches may be used to detect the presence or absence of a skin-print capture and transport unit 1 and/or a reagent cartridge 300.

The skin-print analysis apparatus 100 may comprise a controller for controlling all of the relevant movements, actuations, illuminations and sensor readings required by the skin-print analysis apparatus 100. The controller may comprise components which are integral to the skin-print analysis apparatus 100 and components which are outside the skin-print analysis apparatus 100 such as a third party computer connected to the integral controller by any means such as by a wired or wireless connection.

Reagent Cartridge

Referring to FIG. 4, the reagent cartridge 300 comprises a body 310, one or more waste reservoirs 320 and one or more fluid reservoirs 312, 313 which are pre-filled with one or more fluids comprising one or more reagents and or wash solutions. The fluid or fluids may be liquid.

The reagent cartridge 300 further comprises a sealing surface 316 and one or more channels 315 in the sealing surface 316 for the passage of reagent. The channels 315 are open-topped at the sealing surface 316. The sealing surface 316 is in fluid communication with the one or more fluid reservoirs 312, 313 via one or more dispensing ports 319. The waste reservoir 320 is in fluid communication with the sealing surface 316 via one or more waste ports 321 each connecting one of the channels 315 with the waste reservoir 320.

The sealing surface 316 may be a surface of the body 310 of the reagent cartridge 300 or, alternatively, it may be a discrete layer which is bonded to the body 310 or overmoulded on the body 310. The channels 315 may be etched, moulded or machined. The sealing surface 316 is of a compliant material chosen to seal against the material of the optically transparent substrate 200. Indeed, it is possible that more than just the sealing surface 316 of the reagent cartridge 300 may be of a material sufficiently flexible to assist in forming a seal of the surface with a harder material into which the surface may come into contact in use, as discussed further below.

Prior to use, the sealing surface 316 may be covered with a releasable film or plug to keep the surface 316 clean and to prevent reagent from passing through the dispensing ports 319.

The channels 315 may be wide and shallow in a region intended to come into contact with the optically transparent substrate 200 in order to maximise contract of the reagent in the channels 315 with a skin-print on the optically transparent substrate 200. By wide and shallow, it is meant that the width of the channels 315 is greater than their depth.

The channels 315 can be of any number consistent with obtaining a measurable image of the pore structure across regions of the fingerprint. Different reagents can be used to detect different substances. Different substances of interest may have different concentrations in the skin-prints to be analysed and may have different binding characteristics with the reagents. For substances with a low threshold concentration for detection it is important to maximise the contact of reagent with the substance. The channel profile should therefore be wide to provide the largest area and shallow to reduce the diffusion distance of reagent to the substrate surface, consistent with providing a mechanically robust wall thickness between the channels, which can be moulded accurately and seal the channels effectively. Use of shallow channels also minimises the volume of reagents required for a given velocity of reagent along the channel.

Components of the reagent cartridge 300 may be injection moulded separately and adhered together or co-moulded. Other fabrication methods include 3D printing, composites, cast or pressed metal and vacuum forming etc.

Filling of the reagent cartridge during manufacture may be carried out by applying the fluid through the side comprising the sealing surface 316. The areas around the dispensing ports 319 are raised which enables a filling device to be easily sealed against these areas and reagent delivered into the barrels of the cartridge via the ports. The ports may be sealed by application of a film across all the raised portions.

In the specific embodiment, there are six channels 315. Each of the six channels 315 has an axis of elongation and each of the six axes of elongation is parallel to each of the other axes of elongation. Each of the channels 315 is associated with two fluid reservoirs, a first fluid reservoir 312 and a second fluid reservoir 313. A dispensing port 319 is associated with each fluid reservoir 312, 313. Therefore each channel 315 is associated with two dispensing ports 319, one for each of the two fluid reservoirs 312, 313 with which it is associated. The two dispensing ports 319 associated with each channel 315 are each located on or substantially on the axis of elongation of said channel 315.

Each channel 315 is also associated with a waste port 321. Each waste port 321 is located towards an end of the channel 315 furthest from the dispensing ports 319 and provides fluid communication between the channel 315 and the waste reservoir 320. The waste port 321 for each channel 315 is located on or substantially on the axis of elongation of said channel 315.

The first fluid reservoir 312 for each channel 315 may be intended for reagent while the second fluid reservoir 313 for each channel 315 may be intended for a wash solution.

Figure 10:
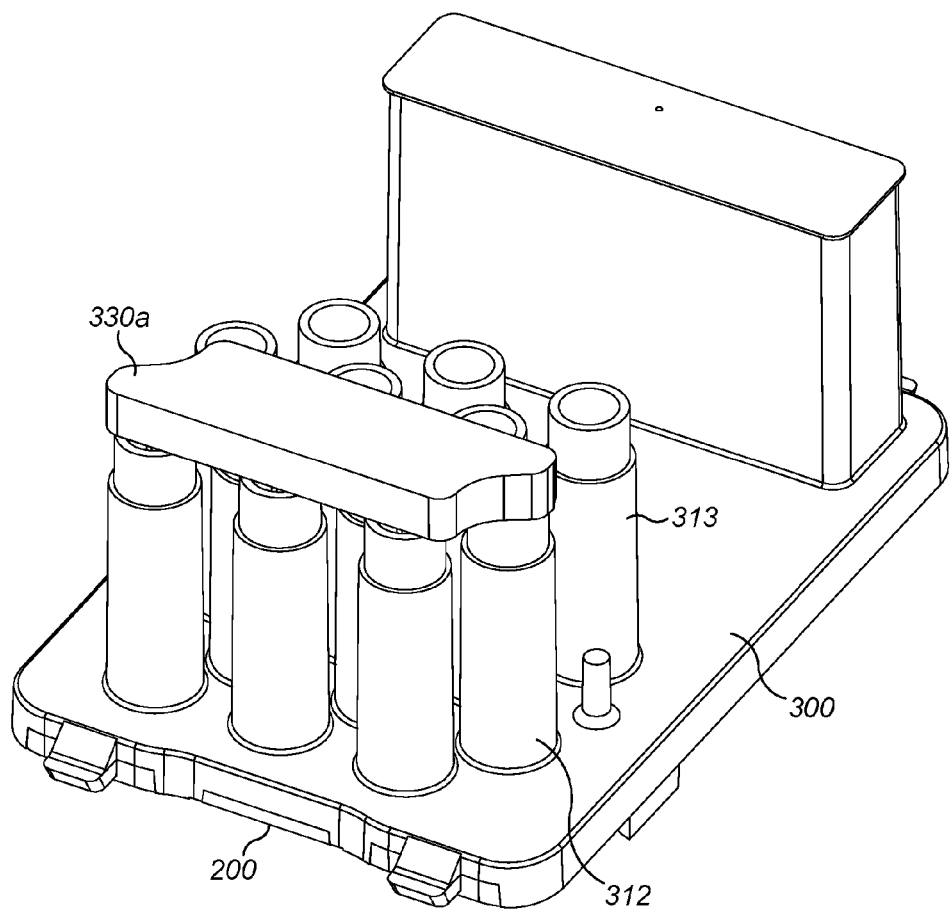
FIG. 10 shows a reagent cartridge for use with the skin-print analysis apparatus, the reagent cartridge including a plurality of fluid reservoirs.
Figure 11:
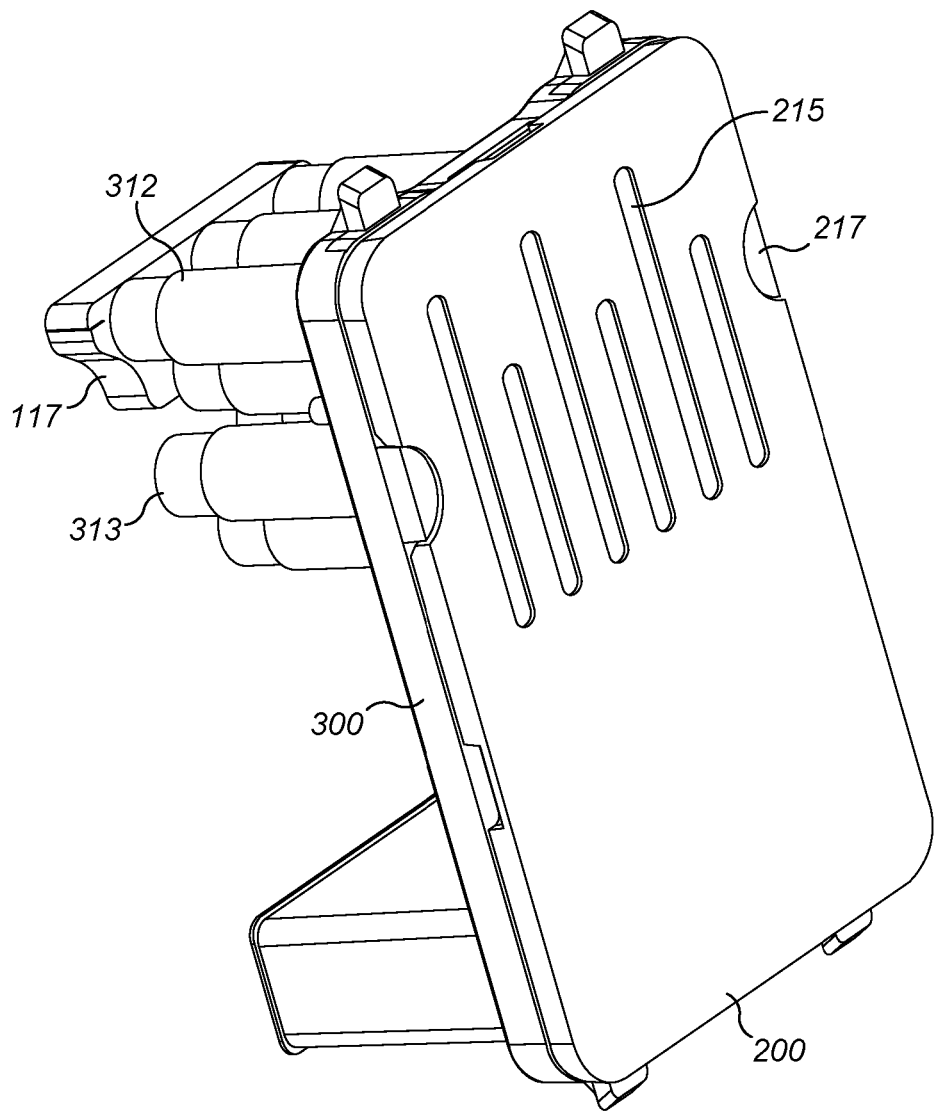
FIG. 11 shows the reagent cartridge of FIG. 10 attached to a skin-print substrate.
Figure 28:
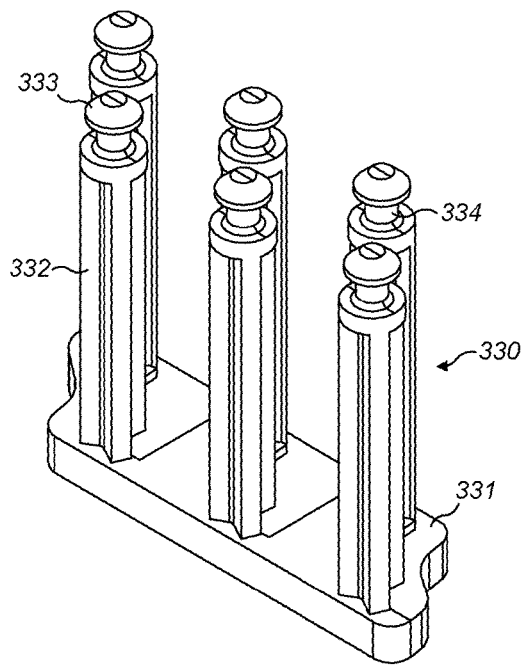
FIG. 28 shows an actuator assembly for use with the reagent cartridge of FIG. 4.

The reagent cartridge 300 comprises a first actuator assembly 330a for actuating all of the first fluid reservoirs 312 and a second actuator assembly 330b for actuating all of the second fluid reservoirs 313. As shown in FIG. 28, each actuator assembly 330 comprises an actuating plate 331 and a plurality of actuators 332. Each actuator is in the form of a piston 332 and each piston 332 comprises a tip 333. The tip 333 may comprise a sealing element such as an O-ring (not shown) mounted in a groove 334. Alternatively, the sealing element may comprise a co-moulded circumferential extension of the tip 333. The sealing element is configured to seal with an internal surface of the fluid reservoir 312, 313 into which the piston 332 is received. The first actuator assembly 330a is shown in FIGS. 10 and 11 in mutual cooperation with the first fluid reservoirs 312.

The actuating plate 331 ensures all pistons 332 connected to the actuating plate 331 are actuated simultaneously. By this method, all of the pistons 332 associated with the first set of fluid reservoirs 312 travel simultaneously and, separately, all of the pistons associated with the second set of fluid reservoirs 313 travel simultaneously. By actuating all fluid reservoirs of the first set of fluid reservoirs simultaneously, this ensures that flow of fluid through each of the first set of six dispensing ports 319 is even such that fluid flows evenly down each of the plurality of channels 315. Similarly, by actuating all fluid reservoirs of the second set of fluid reservoirs simultaneously, this ensures that flow of fluid through each of the second set of six dispensing ports 319 is even such that fluid flows evenly down each of the plurality of channels 315.

Figure 29:
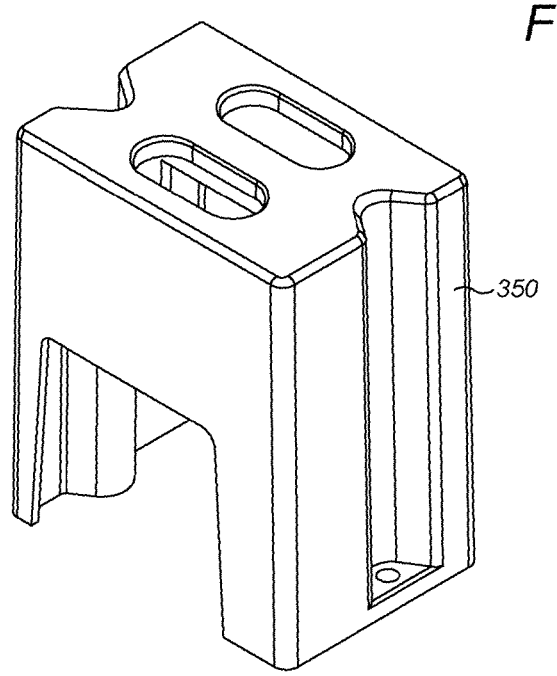
FIG. 29 shows a perspective view of a cap which may be supplied with the reagent cartridge illustrated in FIG. 4.

The reagent cartridge 300 may be supplied with a resilient cap 350, as shown in FIG. 29. The resilient cap 350 is configured to prevent the actuator assemblies 330 from being moved in transit. The resilient cap 350 may be fastened to the reagent cartridge 300 using heat stakes (not shown).

The waste reservoir 320 is intended to receive fluid from the reservoirs 312, 313 after passage over the substrate 200. The waste chamber may contain an absorbent material such as a sponge or silica material to absorb the fluid and prevent it leaking from the cartridge after use.

The reagent cartridge 300 is of a material which exhibits very low or no fluorescence when exposed to radiation of wavelengths used to excite fluorophors in the reagents present in the reservoirs 312, 313 of the reagent cartridge 300. Possible materials for the reagent cartridge 300 include polycarbonates, cyclic olefin co-polymer, PMMA, polypropylene and thermoplastic vulcanisate (TPV) plastics. Suitable grades of such materials may be determined by routine testing for low fluorescence compared to the signal from the fingerprint.

Furthermore, the sealing surface 316 comprises or is coated with a biocompatible material to inhibit non-specific adsorption of reagent.

In the specific embodiment, the six channels 315 of the reagent cartridge 300 are configured to cooperate with six grooves 215 in the substrate 200, as will be discussed further below. Other numbers of channels are contemplated within the scope of this disclosure. It is not necessarily the case that the number of channels 315 of the reagent cartridge is the same as the number of grooves 215 in the substrate 200.

The reagent cartridge 300 further comprises a plurality of lugs 329 on an outer facing edge of the reagent cartridge 300, as shown in FIG. 4. The lugs 329 are configured to be received into a plurality of detents 29 in the inner surface of the frame 20 of the skin-print capture and transport unit 1 adjacent the substrate receiving portion 26, as shown in FIG. 27. In this way, the reagent cartridge 300 may be snap-fitted to the skin-print capture and transport unit 1 in a position where the substrate is flush with a sealing surface 316 of the reagent cartridge 300. The snap-fitting is such that removal of the reagent cartridge 300 from the skin-print capture and transport unit 1 is inhibited. Since the substrate 200 may also be inhibited from being removed from the skin-print capture and transport unit 1, effectively, the reagent cartridge 300 is inhibited from being removed from the substrate 200.

In addition, the reagent cartridge 300 comprises a plurality of semi-circular protrusions 317. These are configured to correspond with, in use, a plurality of semi-circular cutouts 217 in the perimeter of the substrate 200. Their purpose is to ensure correct alignment of the reagent cartridge 300 with the substrate 200.

Optionally, the reagent cartridge 300 may further comprise an identifier (not shown) for identifying the cartridge 300, perhaps to identify the number of channels or to identify the particular reagent or reagents present in the cartridge 300. The identifier may be machine-readable such as a barcode or an RFID tag, or may be any other form of identifying means. The identifier may provide identification unique to the cartridge 300 or it may identify the cartridge 300 as being of a certain type (e.g. specific number of channels and reagent).

In the event that, for example, it is intended to test for two metabolites then it may be that a first half of the first set of fluid reservoirs 312 contains a first reagent and a second half of the first set of fluid reservoirs 312 contains a second reagent. The first half of the first set of fluid reservoirs 312 may alternate with the second half of the first set of fluid reservoirs 312.

In an alternative to the illustrated embodiment, it may be that there is only a single channel 315 supplied by one reagent reservoir 312 and one wash-fluid reservoir 313.

In a further alternative, the reagent cartridge may be configured for use with a planar substrate 200 without grooves 215. In such a case, it may be that each dispensing port 319 of the reagent cartridge 300 opens out directly into a channel 315.

Substrate

In a preferred embodiment, the optically transparent substrate 200 (as shown in FIG. 3) comprises a sample receiving zone 201 for receiving a skin-print and a fluid transmission zone 202 comprising one or more grooves 215 for directing fluid towards the sample receiving zone 201.

In the preferred embodiment, the substrate 200 comprises six grooves 215 to correspond with the six channels 315 of the reagent cartridge 300.

On alignment of the substrate 200 with the reagent cartridge 300, the substrate 200 makes contact with the surface 316 of the reagent cartridge 300 such that each channel 315 of the six channels 315 cooperates with one of the six grooves 215 in order to complete a fluid flow path from both of the dispensing ports 319 associated with the said channel 315 to the said channel 315.

There is effectively one fluid flow path per channel 315, except that each flow path has a bifurcated starting point beginning either in the first fluid reservoir 312 (containing, for example, reagent) or in the second fluid reservoir 313 (containing, for example, wash solution).

The fluid flow path includes the dispensing ports 319 from both fluid reservoirs 312, 313 then subsequently follows the groove 215 parallel with but above the surface 316 before exiting the groove 215 and entering the channel 315 at a first end. The path continues along the channel to a second end where the path passes out of the channel 315 via a waste port 321 into the waste reservoir 320.

The open-topped channels 315 are each configured to be closed by the sample receiving zone 201 of the substrate 200 on which a skin-print may be present. As such, any fluid which passes through the fluid flow path into the channel will make contact with the skin-print when in the channel 315.

The substrate 200 comprises a plurality of detents 228 on an outer edge of the substrate 200, as shown in FIG. 3. The plurality of detents 228 is configured to receive a plurality of corresponding lugs 28 which project from an inner surface of the frame 20 of the skin-print capture and transport unit 1 adjacent the substrate receiving portion 26. In this way, the substrate 200 may be snap-fitted to the skin-print capture and transport unit 1 such that removal of the substrate 200 from the skin-print capture and transport unit 1 is inhibited. This is shown in FIG. 27.

In addition, the substrate 200 comprises a plurality of semi-circular cutouts 217 in the perimeter of the substrate 200. These are configured to correspond with a plurality of semi-circular protrusions 317 in the reagent cartridge 300. Their purpose is to ensure correct alignment of the reagent cartridge 300 with the substrate 200.

In an alternative embodiment (not illustrated) the substrate 200 may be planar without grooves 215. In this case, a reagent cartridge 300 for use with the planar substrate may have dispensing ports 319 which open out directly into a channel 315.

Use of the Skin-Print Analysis Apparatus of the Preferred Embodiment to Analyse a Substrate Skin-Print Capture and Transport Unit In use, the skin-print analysis apparatus 100 begins in an initial configuration as shown in FIG. 1, with a top cover removed.

Figure 12:
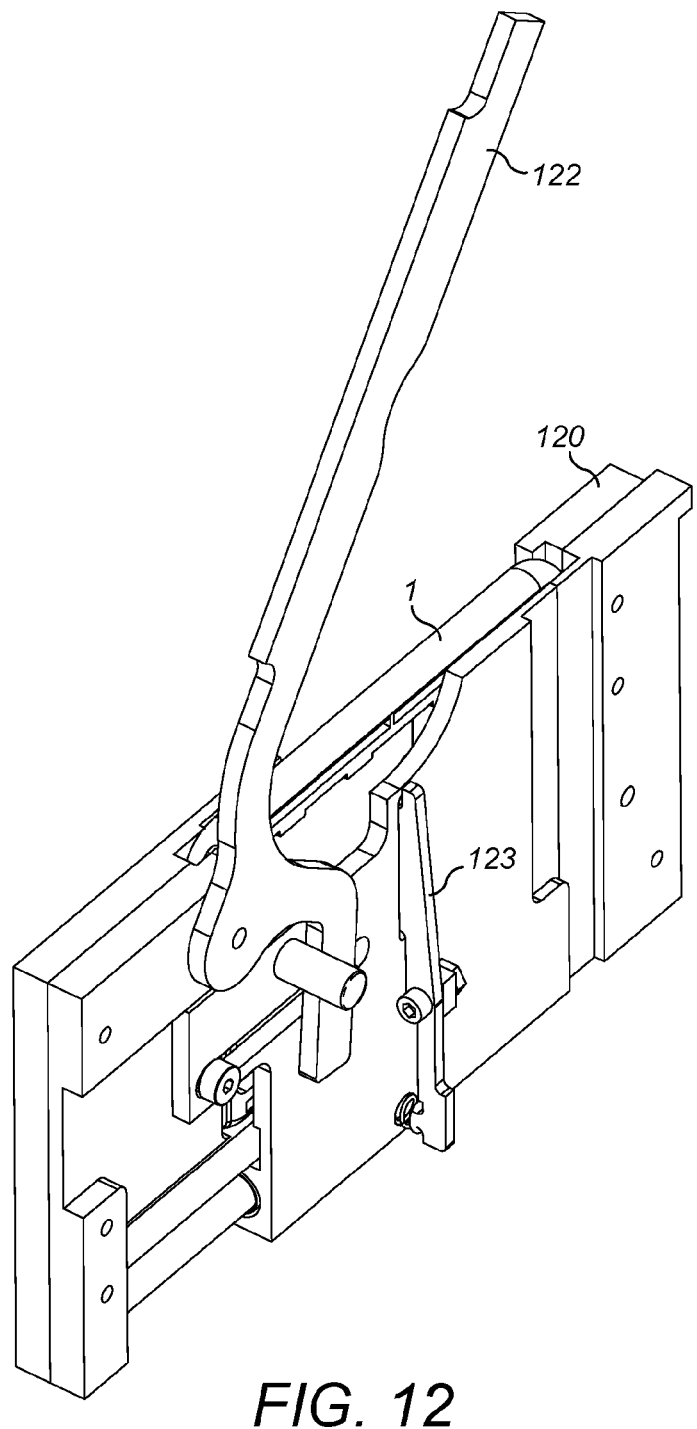
FIG. 12 shows a mechanism for opening the skin-print capture and storage unit, the mechanism being in a first position.
Figure 13:
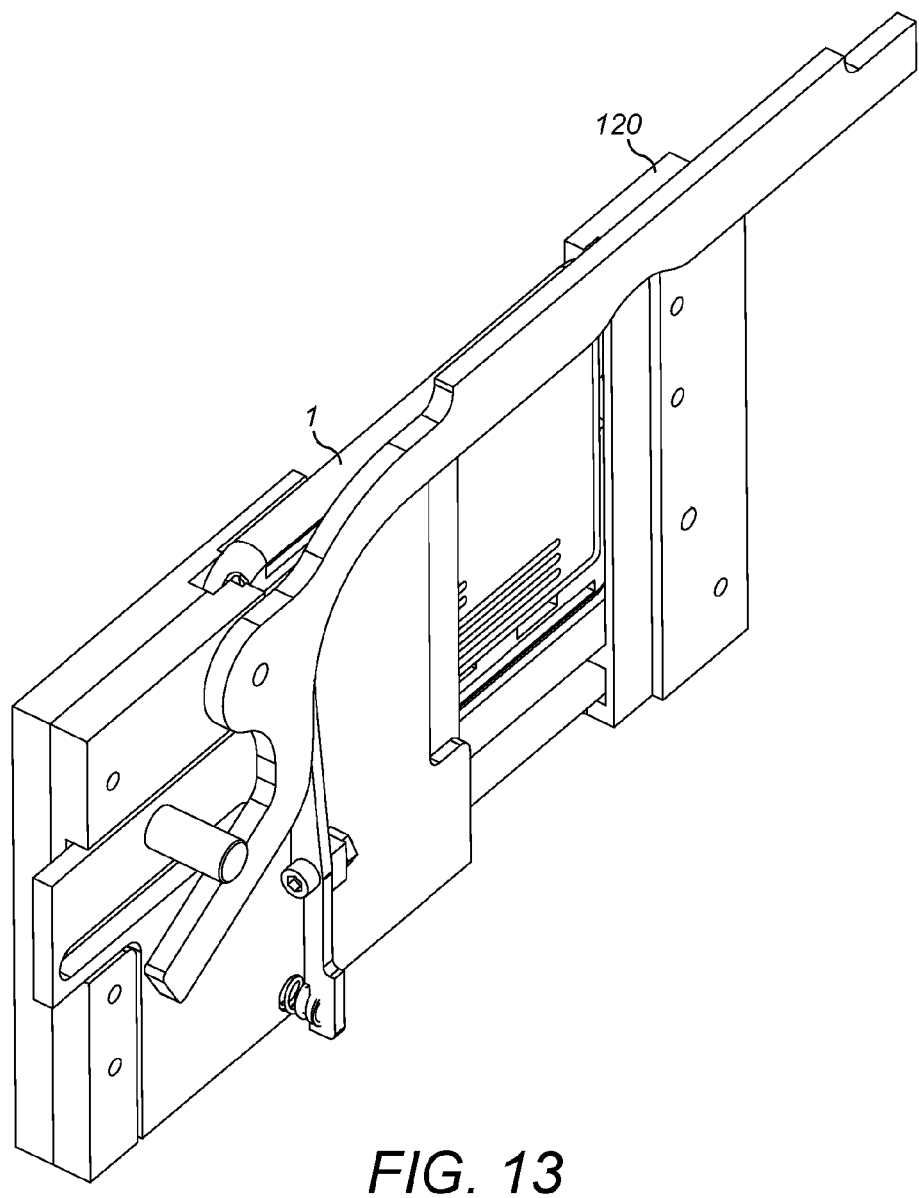
FIG. 13 shows the mechanism of FIG. 12, the mechanism being in a second position.

A user lifts a handle 122 (shown lifted in FIG. 12) in order to open a door (not shown) which provides access to the apparatus from above. A skin-print capture and transport unit 1 containing a substrate 200 is inserted into the holder 120, as shown in FIG. 12. Also, a reagent cartridge 300 is inserted into the cradle 113a of the movable reagent cartridge mount 113, as shown in FIG. 1. The handle 122 of the holder 120 is lowered by a user into a closed position, shown in FIG. 13, in order to actuate opening of the shutters of the skin-print capture and transport unit 1.

An elongate actuator 123 of the holder 120 has a stepped profile. The elongate actuator 123 is positioned to break the frangible element 35 and come to rest in the elongate slot 40 which sits below the broken frangible element. (As illustrated in FIG. 12, the elongate actuator 123 may be mounted on an opposite side of a plate which faces the frangible element 35, with the elongate actuator 123 passing through an aperture in that plate in order to contact the frangible element 35.) The stepped profile of the elongate actuator 123 makes contact with the third pin 39 of the skin-print capture and transport unit 1 and moves the third pin 39 transversely which causes the distal end 35b of the second elongate member 35 also to move transversely. This has the further effect of causing the second pin 32 to move transversely which in turn results in the removal of the second pin 32 from the second detent 24. Thus the retaining mechanism of the skin-print capture and transport unit is disabled by the skin-print analysis apparatus.

Subsequently, the elongate actuator 123 moves in a direction perpendicular to the elongate slot 40 which results in opening of both the shutters 10, 30.

Once the shutters 10, 30 are open, the skin-print capture and transport unit 1 is moved by the holder 120 in a direction orthogonal to the aperture 121 such that a back surface of the substrate 200 makes contact with the quartz window in the aperture 121.

Figure 7:
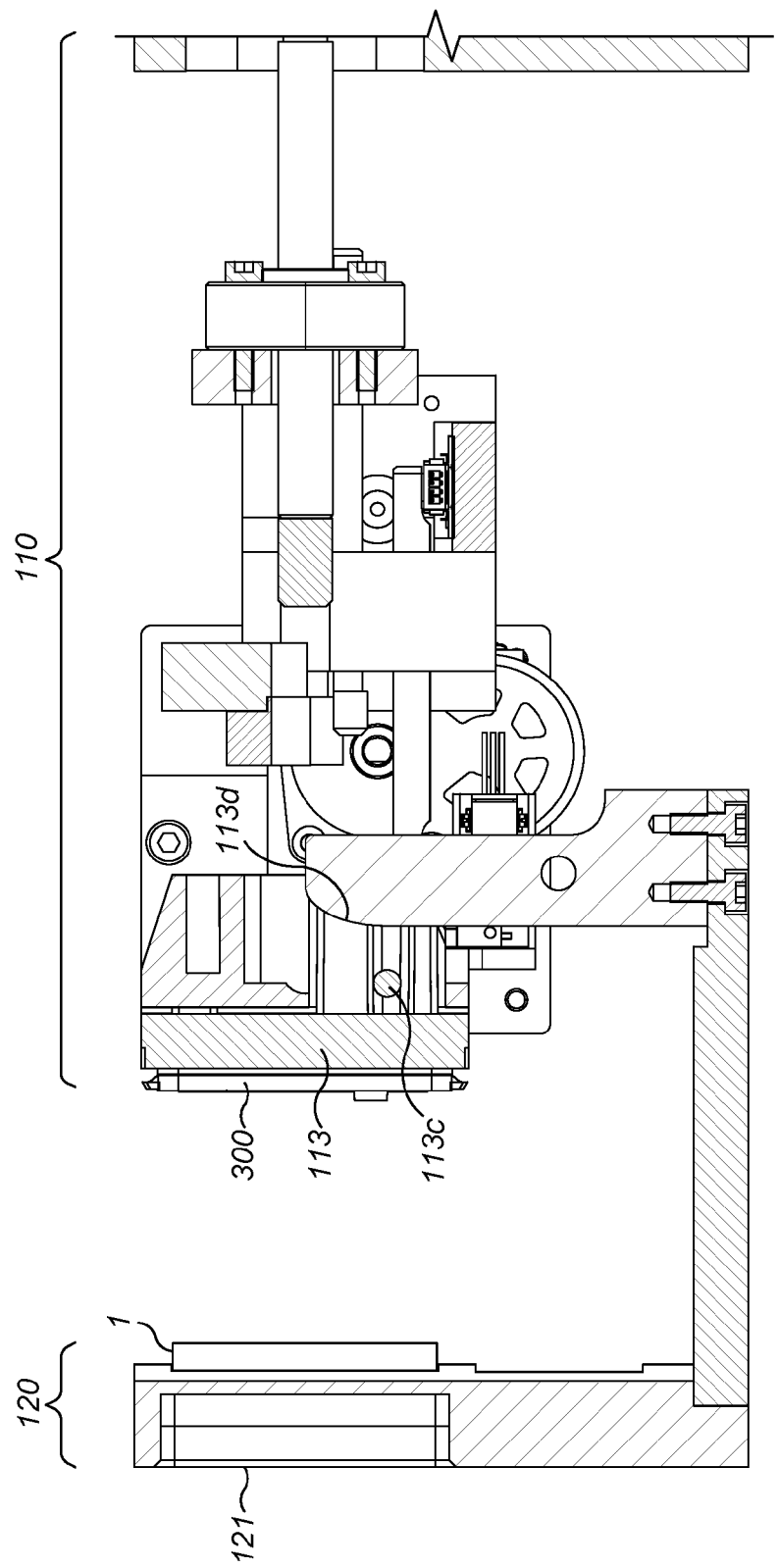
FIG. 7 shows the holder and the reagent supply assembly of the skin-print analysis apparatus of FIGS. 1 and 2 in an intermediate configuration in which the reagent cartridge has been rotated through 90°.

Next, a controller actuates movement of the stepper motor 112 which, initially, causes the movable reagent cartridge mount 113 to rotate through 90° to the position shown in FIG. 7 whereby the sealing surface of the reagent cartridge 300 is approximately parallel to the substrate 200 and the quartz window in the aperture 121.

In this position the reagent cartridge 300 is at a distance from the sensor 140 such that it is outside the focal range of the sensor 140. The illumination radiation source 135 illuminates the substrate 200, preferably with broadband white light or coloured light having a narrow range of wavelengths. The sensor 140 then detects an image of the broadband white light reflected by the substrate 200. Optionally, there may be a lens to focus the reflected light before it reaches the sensor 140. An algorithm may check that a skin-print is detected on the substrate 200. In the event that no skin-print is detected on the substrate, the movable reagent cartridge mount 113 may revert to the initial position for removal of the skin-print capture and transport unit 1. This prevents analysis of a substrate which will not yield any useful results and also means that a reagent cartridge 300 is not used where no useful result will be obtained.

In the event that a skin-print is detected on the substrate, the stepper motor 112 continues its rotation which, now that the rotation of the moveable reagent cartridge mount 113 is complete, causes the movable reagent cartridge mount 113 to move laterally towards the substrate 200.

After sufficient lateral movement, the plurality of semi-circular protrusions 317 of the reagent cartridge 300 cooperate with the plurality of semi-circular cutouts 217 in the perimeter of the substrate 200 to ensure correct alignment of the reagent cartridge 300 with the substrate 200.

On further lateral movement, the sealing surface 316 of the reagent cartridge 300 comes into contact with the front surface of the substrate 200 on which a finger-print is present.

Given the alignment provided by the interaction of the semi-circular features, the reagent cartridge 300 meets with the front surface of the substrate such that the channels 315 in the sealing surface 316 cooperate with grooves 215 in the fluid transmission zone 202 of the optically transparent substrate 200 to form fluid flow paths, as described above.

Figure 15:
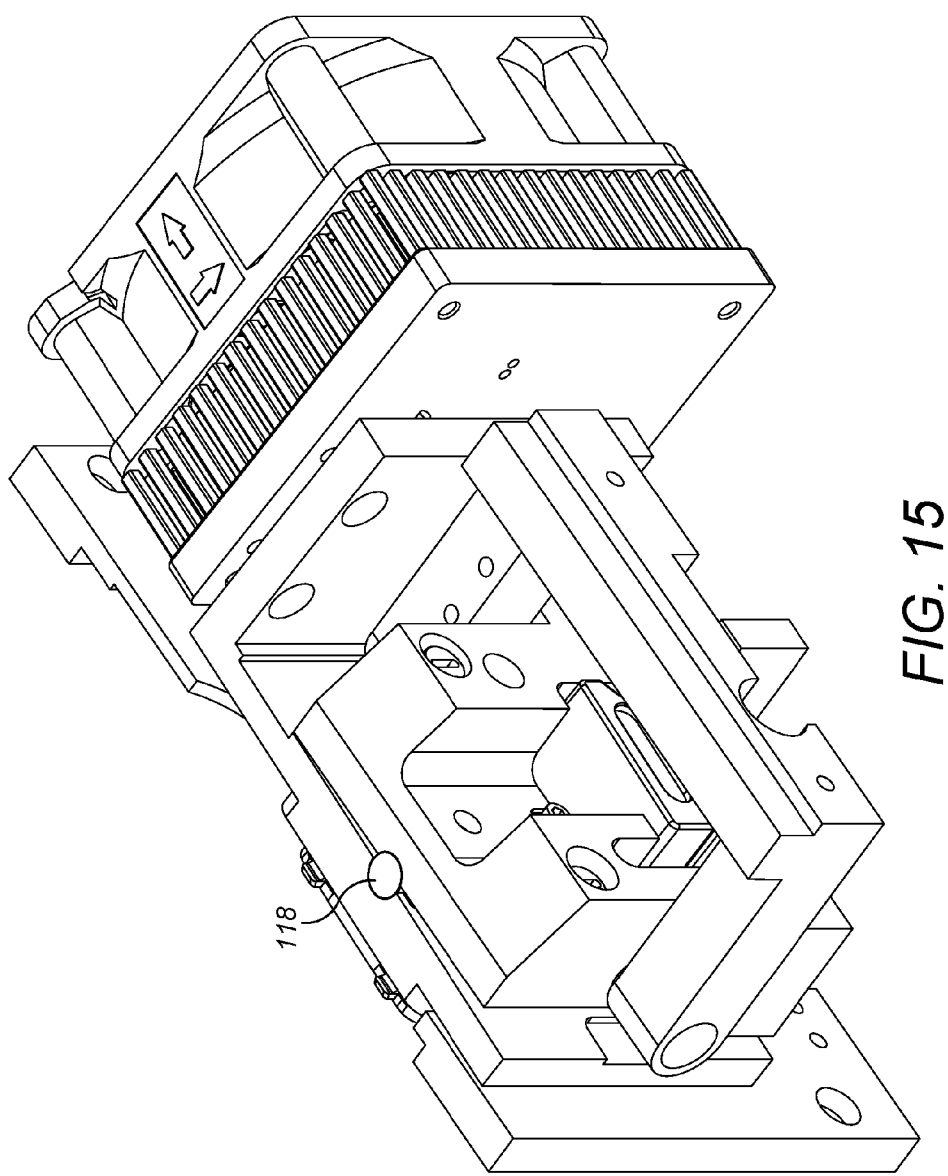
FIG. 15 shows the mechanism of FIG. 14 viewed from a front side, the mechanism being in the second position.

Given the number of moving parts, on initial contact of the sealing surface 316 with the substrate 200, it may be that the sealing surface 316 of the reagent cartridge 300 is not exactly parallel with the substrate 200. The cradle 113a is mounted on a pivot 118 (see FIG. 15) to allow some limited left-right rotational movement. Similarly, limited rotational up-down movement is made possible since the 90° rotation allows for some over/under rotation. By these features, the plane of the sealing surface 316 of the reagent cartridge 300 is adjustable so that, with further movement of the stepper motor 112, the sealing surface 316 becomes parallel with the substrate 200. There may be pairs of springs acting either side of a vertical rotational axis and either side of a horizontal rotational axis by which an even approach of the sealing surface 316 towards the substrate 200 is achieved.

Once the sealing surface 316 meets with the substrate 200, the lugs 329 are received into the plurality of detents 29 in the inner surface of the frame 20 of the skin-print capture and transport unit 1. In this way, the reagent cartridge 300 is snap-fitted to the skin-print capture and transport unit 1.

Movement of the stepper motor 112 continues until the force exerted by the sealing surface 316 on the substrate is approximately 200 N. At this point, the sealing surface 316 is in close contact with the substrate 200 and the skin-print analysis apparatus 100 is in the analysis configuration.

In this position, the sealing surface 316 makes a seal with the front surface of the substrate 200 such that the open-topped channels 315 of the sealing surface 316 are closed by the substrate 200. Furthermore, the grooves 215 in the substrate 200 are aligned with and in fluid communication with the dispensing ports 319. The grooves 215 in the substrate 200 cooperate with the channels 315 in the sealing surface 316 to provide a route for fluid from the reservoirs 312, 313 to those parts of the front surface of the substrate on which the skin-print is located.

Some of the fluid reservoirs 312, best shown in FIG. 10, are pre-filled with one or more reagents. Others of the fluid reservoirs 313 are filled with wash solution, buffer solution, water or another fluid for flushing the channels.

Once a seal is made between the sealing surface 316 and the substrate 200, one or more of the actuator assemblies 330 is actuated by the actuator driver (not shown) to force fluid out of the respective reservoirs 312, 313, through the respective dispensing ports 319 via the grooves 215 and into the respective channels 315. Normally only one actuator assembly 330 will be actuated at a time. By virtue of the seal with the front surface of the substrate 200, fluid dispensed from the dispensing ports 319 is retained within the channels 315. Reagent (or wash solution) therefore comes into intimate contact with the front surface substrate 200 on which a skin-print was previously applied. The one or more reagents therefore make contact with the chemicals present in the skin-print, including any metabolites which are present.

In the preferred embodiment, the first set of reservoirs 312 contain reagent and the second set of reservoirs 313 contain a wash fluid (e.g. water). The actuator assembly 330 associated with the first set of reservoirs 312 is actuatable independently from the actuator assembly 330 associated with the second set of reservoirs 313. In this way, use of the first actuator assembly 330a forces reagent into all the channels simultaneously and use of the second actuator assembly 330b forces wash into all the channels simultaneously.

The actuator assemblies 330 can be actuated independently and alternately by a single actuator driver. The actuator driver comprises a stepper motor 112 driving a cam which is engagable with the both actuator assemblies 330a, 330b such that when the stepper motor 112 is rotated in one direction it actuates the reagent-filled reservoirs 312 and when rotated in the opposite direction is actuates the wash-filled reservoirs 313. By controlling the rotation and direction of the stepper motor 112, reagent and wash can be controlled independently.

The reagent may be chosen to bind with a particular substance which may be present in the skin-print. In the event that the particular substance is present then the reagent will bind with it. In the event that the particular substance is absent then the reagent will not bind with it.

After a pre-defined period, the second set of fluid reservoirs 313 (containing wash fluid) is actuated. This causes wash fluid to travel through the channels 315. In the event that the reagent has bound with the substance then the flow of wash fluid will not affect this, but excess reagent which may be non-specifically adsorbed to the substrate surface and not bound to the substance will be washed away, leaving only bound reagent. In the event that the substance is absent such that no binding has occurred then the wash fluid will cause all of the non-specifically adsorbed reagent to be flushed through the channels 315. In either event, excess fluid is collected in the waste reservoir 320 which is in fluid communication with an end of the channels 315 opposite those ends which receive the fluid from the fluid reservoirs 312, 313.

The excitation radiation source 130 is configured to emit electromagnetic radiation within a specific range of wavelengths. The wavelength of the electromagnetic radiation may be chosen in combination with the one or more reagents for detecting one or more specific substances. Electromagnetic radiation in the ultra violet region of the electromagnetic spectrum may be used.

The excitation radiation excites electronic transitions in the reagent. Therefore, if the substance is present in the skin-print such that the reagent is present (having been bound to the substance) then the reagent will be caused to emit fluorescence radiation at a different wavelength from that of the excitation radiation.

The sensor 140 is configured to receive the fluorescence radiation emitted by the skin-print. Standard techniques for analysis of the fluorescence radiation may be employed in order to determine the presence or absence of one or more specific metabolites from the skin-print.

An optical filter can be placed between the substrate and the detector to eliminate scattered excitation light. For example, a long pass wavelength filter to exclude the excitation light from the CCD array, or optionally a band pass wavelength filter to pass only fluorescent light from the surface may be used. In the case of a single compound binding to the substance, one filter may be used. In the case of more than one reagent each containing one compound which fluoresces at a different wavelength, a long filter may be used to remove excitation light, and the captured image consists of a series of stripes of light at different wavelengths corresponding to different compounds binding to the substance in the different channels. Image processing can then be used to detect the presence or analyse the intensities of the different stripes.

The skin-print analysis apparatus may comprise or be associated with image capture and display software to display the fluorescent image, or algorithms written in software to analyse the fingerprint image and extract information concerning the presence or absence of suspected chemicals and the identification of high levels of fluorescence with the pore structure of the print.

Preferably the image analysis includes detection of the pore structure of the print and conformation of the presence of fluorescent signal associated with the pore structure and not the background. Alternately the fluorescent image may be displayed and visually inspected for the presence of fluorescence and pore structure.

The fluorescent image comprises one or more areas of colour or their absence at the position of each of the channels 315. The presence of an area confirms the presence of a fluorophor bound to a metabolite in the fingerprint, and the presence of the fluorophors on the pore structure.

Standard techniques for the analysis of skin-prints may be used to determine the identity of subject who provided the skin-print. For example, the optical image of the skin-print may be compared with a database of skin-prints, each of which skin-prints is associated with an individual subject. The analysis may determine the identity of a subject by confirming a match between an entry in the database and the optical image obtained.

By this method, it is possible simultaneously to confirm the presence of one or more particular metabolites in a skin-print and to confirm the identity of the subject who provided the skin-print.

Once the analysis is complete, the skin-print analysis apparatus 100 returns to its initial configuration largely by reversing the steps adopted to arrive at the analysis configuration. However, given the snap-fitting of the reagent cartridge 300 to the skin-print capture and transport unit 1, even once the 200 N force is no longer applied and the stepper motor returns the analysis apparatus to the start configuration, the reagent cartridge 300 is effectively fixedly attached to the substrate 200 via the skin-print capture and transport unit 1. The reagent cartridge 300 does not, therefore, return in the cradle 113a when the cradle 113a returns to the initial configuration.

Since the reagent cartridge 300 is fixedly attached to the substrate 200 via the skin-print capture and transport unit 1, effectively forming a single unit, the channels 315 remain sealed even after the force ceases to be applied when the apparatus returns to the initial configuration. This means that fluids are contained within the single unit and there is significantly reduced likelihood of fluid escaping and perhaps contaminating any apparatus.

In the explicitly described embodiments, the reagent cartridge 300 is a consumable item. The reagent cartridge 300 may be supplied ready for use with the fluid reservoirs 312, 313 pre-filled with one or more reagents and/or wash fluids. In this way, a user may keep in stock a variety of reagent cartridges 300 filled with a variety of different reagents and may select the cartridge on the basis of one or more specific metabolites for which a particular test is intended to detect, depending on the circumstances.

Once the analysis is complete the substrate 200 and reagent cartridge 300 may be removed from the skin-print capture and transport unit 1 as a single item for archiving, storage or disposal, or remeasured for forensic purposes The bound reagent will retain its fluorescent activity for some time so that later verification of an initial result is possible. Since the single unit is effectively sealed from the external environment, any attempt to tamper with the substrate is likely to be immediately obvious. If no longer required, the reagent cartridge 300 may be removed from the substrate 200 and remanufactured or reconditioned for subsequent use.

Reagents, Binding and Fluorescence

The skilled person will readily appreciate that neither the analysis apparatus 100 nor the reagent cartridge 300 is restricted to any particular reagents or types of reagent. The reagent or reagents must simply be capable of being dispensed from the reagent cartridge 300 into the channels 315 whereby it or they can come into contact with the sample receiving zone 201 of the substrate 200.

Some purely exemplary reagents for use with the present invention are described in WO 2007110605. This document also explains the processes by which reagents may bind to particular metabolites which may be present in a skin-print (such as a fingerprint) as well as possible fluorophors which may be suitable for use with particular reagents.

WO 2007110605 describes a method for the fluorescent detection of a substance, the method comprising providing particles comprising a metal or a metal oxide core, wherein one or more optionally fluorescently tagged antibodies or human specific peptide nucleic acid (PNA) oligomers for binding to a substance is/are bound, directly or indirectly, to the surface of the metal or metal oxide; contacting a substrate, which may or may not have the substance on its surface, with the particles for a time sufficient to allow the antibody/PNA oligomer to bind with the substance; removing those particles which have not bound to the substrate; if the antibodies or PNA oligomers are not fluorescently tagged, contacting the substrate with one or more fluorophors that selectively bind with the antibody and/or substance, then optionally washing the substrate to remove unbound fluorophors; and illuminating the substrate with appropriate radiation to show the fluorophors on the substrate.

Use of the Skin-Print Capture and Transport Unit for Capturing a Skin-Print

For completeness, the following is a description of how the skin-print capture and transport unit 1 (discussed with reference to the preferred embodiment of the skin-print analysis apparatus 100) is used to collect a skin-print.

The skin-print capture and transport unit 1 is supplied with the front shutter 10 in the first closed position and the rear shutter in the closed position.

In order to receive a skin-print, the front shutter 10 is manually moved with respect to the frame 20 from the first closed position into the first open position. A user may effect this movement by sliding the front shutter 10 using the thumb grip 18. In the first open position, the front surface of the substrate contained within the substrate receiving portion 26 of the frame 20 is accessible through the open front shutter 10. A skin-print may then be received onto the front surface of the substrate.

Once the skin-print impression has been left on the front surface of the substrate, the front shutter 10 may be moved with respect to the frame 20 into the second closed position. The second closed position prevents the front shutter 10 from being re-opened by sliding the front shutter 10 with respect to the frame 20. This is because, as previously explained, the diamond-shaped first pin 31 is received into the first detent 17 and is retained in the first detent 17 which results in the front shutter 10 being fixed with respect to the rear shutter 30 to which the first pin 31 is fixedly attached.

Non-Essential and Alternative Features

The following is a non-exhaustive list of non-essential and alternative features which fall within the scope of the disclosure.

As mentioned previously, it is not essential to the invention that the substrate 200 for analysis is housed in a skin-print capture and transport unit 1. Even in the event that the substrate is housed in skin-print capture and transport unit 1, it need not be of the kind described herein. For example, there may be a skin-print capture and transport unit comprising only one shutter. For many applications—including those having an opaque substrate—a single shutter may suffice.

Furthermore, where a skin-print capture and transport unit 1 is used, the particular arrangements of channels, grooves and detents are not essential to the invention. Where the skin-print capture and transport unit is of a different configuration to that described herein, features thereof may be appropriately modified specifically to cooperate with particular the skin-print analysis apparatus 100.

The particular arrangement of six channels 315 and six grooves 215 is not an essential feature of the invention. There may be any number of channels and any number of grooves. The number of channels need not be equal to the number of grooves. For example, multiple channels may share a single groove or multiple grooves may share a single channel. The channels and grooves need not necessarily be of consistent width, either along their length or relative to each other. There may be only a single channel. Where multiple channels are present it may be that different reagents are supplied to different channels. It is possible that there may be more than two fluid reservoirs per channel. For example, for each channel there may be a first reagent reservoir for a first reagent, a second reagent reservoir for a second reagent and a third reagent reservoir for a wash solution. In short, it is essential only that fluid can be dispensed from the fluid reservoir(s) and come into contact with the skin-print on the substrate. The precise arrangement of fluid flow paths of the preferred embodiment is not essential.

The form of tamper-evident features used in the context of the invention is not to be considered limited to those explicitly disclosed herein. For an embodiment having a tamper-evident feature it is necessary only that evidence of unauthorised use or tampering is provided, in any form. The evidence may be immediately visually obvious to a user (i.e. where a mechanical feature of a component is damaged) or it may not be immediately visually obvious. One example of a variant where triggering of a tamper evident feature would not be immediately obvious might involve electronic circuitry in the skin-print capture and transport unit. The electronic circuitry might change state in the event of a shutter of the skin-print capture and transport unit being opened after a skin-print has been received. In this case, when the skin-print capture and transport unit is received into the skin-print analysis apparatus, the apparatus may detect the changed state of the electronic circuitry and thereby detect evidence of the tamper evident feature having been triggered.

In the preferred embodiments, various means for fastening and/or aligning the skin-print capture and transport unit 1, the substrate 200 and the reagent cartridge 300 are described. In the preferred embodiments, these include protrusions, lugs and cutouts. The invention is not, however, to be considered as being limited to these specific implementations for fastening and/or aligning. The skilled person will readily appreciate that other alignment and fastening and sealing features are contemplated within the scope of the disclosure.

The invention claimed is:

1. A method of analysing a skin-print provided on a first surface of an optically transparent substrate, the method comprising the steps of:

retaining the optically transparent substrate bearing a skin-print in fluid communication with a reagent cartridge so as to form a fluid-tight flow path between the first surface of the optically transparent substrate and the reagent cartridge;

exposing the skin-print on the first surface of the optically transparent substrate to one or more reagents from the reagent cartridge, said one or more reagents being selected to bind with one or more metabolites present in the skin-print;

transmitting electromagnetic radiation onto the skin-print through the optically transparent substrate using a radiation source to thereby produce an optical signal of said one or more reagents and/or said one or more metabolites, wherein the electromagnetic radiation comprises visible light to illuminate the skin-print; and detecting a first optical image of the optical signal through the optically transparent substrate using a sensor while the skin-print is illuminated by the visible light.

2. The method of claim 1 wherein the one or more reagents comprise or consist of a fluorescent substance, the method further comprising:

transmitting radiation selected to excite the fluorescent substance through the optically transparent substrate; and obtaining a second optical image of the skin-print while transmitting the radiation.

3. The method of claim 1 wherein the optically transparent substrate is provided within a skin-print capture and transport unit having a retaining mechanism for preventing access to the optically transparent substrate, the retaining mechanism being disablable, the method further comprising a step of:

disabling the retaining mechanism in order to access the optically transparent substrate.

4. The method of claim 3 wherein the skin-print capture and transport unit comprises a tamper-evident feature associated with the retaining mechanism, the method further comprising a step of triggering the tamper-evident feature in order to disable the retaining mechanism.

5. The method of claim 3, further comprising removing the optically transparent substrate and the reagent cartridge as a single unit from the skin-print capture and transport unit, the single unit being available for one of: archiving, storage, and disposal.

6. The method of claim 1, further comprising
confirming a presence of the one or more metabolites present in the skin-print; and
confirming an identity of a subject who provided the skin-print.

7. The method of claim 1, further comprising
receiving the reagent cartridge on a reagent supply assembly, the reagent cartridge containing the one or more reagents prior to a single analysis; and
removing the reagent cartridge following a single analysis.

8. The method of claim 7, wherein the reagent cartridge comprises one or more channels for the passage of reagent.

9. The method of claim 8, further comprising forcing reagent to flow out of one or more fluid reservoirs into the one or more channels.

* * * * *